(12) United States Patent
Mincer et al.

(10) Patent No.: US 9,820,967 B2
(45) Date of Patent: Nov. 21, 2017

(54) METHODS AND COMPOSITIONS FOR INCREASING ANTIBIOTIC ACTIVITY

(71) Applicant: Woods Hole Oceanographic Institution, Woods Hole, MA (US)

(72) Inventors: Tracy Mincer, Falmouth, MA (US); Kristen Whalen, North Falmouth, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 136 days.

(21) Appl. No.: 14/797,951

(22) Filed: Jul. 13, 2015

(65) Prior Publication Data

US 2016/0015686 A1  Jan. 21, 2016

Related U.S. Application Data

(60) Provisional application No. 62/026,351, filed on Jul. 18, 2014.

(51) Int. Cl.
*A61K 31/4015* (2006.01)
*A61K 45/06* (2006.01)
(Continued)

(52) U.S. Cl.
CPC ........ *A61K 31/4015* (2013.01); *A61K 31/165* (2013.01); *A61K 31/43* (2013.01); *A61K 31/431* (2013.01); *A61K 31/496* (2013.01); *A61K 31/5383* (2013.01); *A61K 31/545* (2013.01); *A61K 31/65* (2013.01);
(Continued)

(58) Field of Classification Search
None
See application file for complete search history.

(56) References Cited

PUBLICATIONS

Yalçin, F. N. (2007). Biological activities of the marine sponge Axinella. Hacettepe University Journal of the Faculty of Pharmacy, 27(1), 47-60.*

(Continued)

*Primary Examiner* — Shaojia Anna Jiang
*Assistant Examiner* — Dale R Miller
(74) *Attorney, Agent, or Firm* — Melissa Hunter-Ensor; Elbert Chiang; Greenberg Traurig, LLP

(57) ABSTRACT

One aspect of the invention provides a method of inhibiting an efflux pump in a bacteria, the method comprising contacting the bacteria with 3,4-dibromopyrrole-2,5-dione, thereby inhibiting the efflux pump. Another aspect provides a method of inhibiting proliferation of a bacteria, the method comprising contacting the bacteria with 3,4-dibromopyrrole-2,5-dione and an antibiotic, thereby inhibiting the proliferation of the bacteria. Another aspect of the invention provides a method of increasing the efficacy of an antibiotic, the method comprising contacting a bacteria with 3,4-dibromopyrrole-2,5-dione and an antibiotic, thereby increasing the efficacy of the antibiotic. Another aspect provides a method of inhibiting development of antibiotic resistance in a bacteria, the method comprising contacting the bacteria with 3,4-dibromopyrrole-2,5-dione and an antibiotic, thereby inhibiting development of resistance to the antibiotic. Another aspect of the invention provides a pharmaceutical composition for treating a bacterial infection comprising an effective amount of 3,4-dibromopyrrole-2,5-dione in a pharmaceutically acceptable excipient.

19 Claims, 14 Drawing Sheets

(51) Int. Cl.
  A61K 31/165    (2006.01)
  A61K 31/7048   (2006.01)
  A61K 31/496    (2006.01)
  A61K 31/5383   (2006.01)
  A61K 31/7036   (2006.01)
  A61K 31/431    (2006.01)
  A61K 31/65     (2006.01)
  A61K 31/43     (2006.01)
  A61K 31/545    (2006.01)
  A61K 31/7052   (2006.01)

(52) U.S. Cl.
  CPC ...... *A61K 31/7036* (2013.01); *A61K 31/7048* (2013.01); *A61K 31/7052* (2013.01); *A61K 45/06* (2013.01)

(56) References Cited

PUBLICATIONS

Mahboobi, S., Eichhorn, E., Popp, A., Sellmer, A., Elz, S., & Möllmann, U. (2006). 3-Bromo-4-(1H-3-indolyl)-2, 5-dihydro-1H-2, 5-pyrroledione derivatives as new lead compounds for antibacterially active substances. European journal of medicinal chemistry, 41(2), 176-191.*

Bowman, J., "Bioactive Compound Synthetic Capacity and Ecological Significance of Marine Bacterial Genus *Pseudoalteromonas*," Marine Drugs, vol. 5, pp. 220-241 (2007).

Holmstrom, C. et al., "Marine *Pseudoalteromonas* species are associate with higher organisms and produce biologically active extracellular agents," FEMS Microbiology Ecology, vol. 30, pp. 285-293 (1999).

Kourtesi, C. et al., "Microbial Efflux Systems and Inhibitors: Approaches to Drug Discovery and the Challenge of Clinical Implementation," The Open Microbiology Journal, vol. 7, (Supp. 1-M3), pp. 34-52 (2013).

Opperman, T. J. et al., "Characterization of a Novel Pyranopyridine Inhibitor of the AcrAB Efflux Pump of *Escherichia coli*," Antimicrobial Agents and Chemotherapy, vol. 58, pp. 722-733 (2014).

Rao, D. et al., "Competitive Interactions in Mixed-Species Biofilms Containing the Marine Bacterium *Pseudoalteromonas tunicata*," Applied and Enviromental Microbiology, pp. 1729-1736 (2005).

Stavri, M. et al., "Bacterial efflux pump inhibitors from natural sources," Journal of Antimicrobial Chemotherapy, vol. 59, pp. 1247-1260 (2007).

Tsukamoto, S. et al., "Four New Bioactive Pyrrole-Derived Alkaloids from the Marine Sponge *Axinells brevistyla*," J. Nat. Prod., vol. 64, pp. 1576-1578 (2001).

Vynne, N. et al., "Bioactivity, Chemical Profiling, and 16S rRNA-Based Phylogeny of Pseudoalteromonas Strains Collected on a Global Research Cruise," Mar Biotechnol, vol. 13, pp. 1062-1073 (2011).

Wright, G. "Something old, something new: revisiting natural products in antibiotic drug discovery," Can. J. Microbiol., vol. 60, pp. 147-154 (2014).

* cited by examiner

| compound (μg/mL) | accumulation | | | | efflux | |
|---|---|---|---|---|---|---|
| | AG100[b] mean (RFU)[a] | SD | AG100A[c] mean (RFU)[d] | SD | AG100[b] mean (RFU)[a] | SD |
| 1 (64) | 1280*** | 20 | 1090 | 10 | −68*** | 54 |
| 1 (16) | 1170*** | 8 | 1100 | 14 | −34*** | 58 |
| 1 (4) | 1130*** | 11 | 1200 | 8 | −101*** | 34 |
| 1 (1) | 1010*** | 4 | 1070 | 5 | −247*** | 30 |
| 1 (0.25) | 796*** | 12 | 1080 | 17 | −351*** | 7 |
| 1 (0.06) | 758 | 9 | 1020 | 15 | −422* | 37 |
| Hoechst only | 746 | 16 | 1040 | 10 | −472 | 13 |

FIG. 6

METHODS AND COMPOSITIONS FOR INCREASING ANTIBIOTIC ACTIVITY

CROSS REFERENCE TO RELATED APPLICATIONS

This application is a U.S. Utility application, which claims the benefit of and priority to U.S. Provisional Application Ser. No. 62/026,351, filed Jul. 18, 2014, the contents of which are incorporated herein by reference.

STATEMENT OF RIGHTS TO INVENTIONS MADE UNDER FEDERALLY SPONSORED RESEARCH

This work was supported by the following grant from the National Institutes of Health, Grant No: 1R15AI093158-01. This work was also supported by the following grants from the National Science Foundation, Grant Nos: OCE-1155671 and EPS-1004057. The government has certain rights in the invention.

BACKGROUND OF THE INVENTION

The emergence of multidrug resistant pathogens has become a substantial threat to treating infectious disease. Twenty percent of all deaths globally are the result of bacterial infections, and hospital-acquired infections are the sixth leading cause of mortality in the U.S., with 23 000 deaths per year due to multidrug resistant infections in the U.S. alone. Multidrug-resistant Gram-negative pathogens account for nearly 70% of infections in intensive care units in the U.S. Alarmingly, many Gram-negative clinical strains are becoming resistant to nearly all antibiotics, leaving few antibiotics in the therapeutic repertoire to treat these infections. Consequently, developing new compounds and combinations for the treatment of multidrug resistant pathogens is urgently required.

SUMMARY OF THE INVENTION

As described below, the present invention features the use of 3,4-dibromopyrrole-2,5-dione for increasing antibiotic activity against multidrug resistant bacteria.

In one aspect, the present invention provides a method of inhibiting an efflux pump in a bacteria, the method involving contacting the bacteria with 3,4-dibromopyrrole-2,5-dione, thereby inhibiting the efflux pump.

In another aspect, the present invention provides a method of inhibiting proliferation of a bacteria, the method involving contacting the bacteria with 3,4-dibromopyrrole-2,5-dione and an antibiotic, thereby inhibiting the proliferation of the bacteria.

In another aspect, the present invention provides a method of inhibiting survival of a bacteria, the method involving contacting the bacteria with 3,4-dibromopyrrole-2,5-dione and an antibiotic, thereby inhibiting the survival of the bacteria.

In yet another aspect, the present invention provides a method of increasing the efficacy of an antibiotic, the method involving contacting a bacteria with 3,4-dibromopyrrole-2,5-dione and an antibiotic, thereby increasing the efficacy of the antibiotic.

In another aspect, the present invention provides a method of inhibiting development of antibiotic resistance in a bacteria, the method involving contacting the bacteria with 3,4-dibromopyrrole-2,5-dione and an antibiotic, thereby inhibiting the development of resistance to the antibiotic.

In various embodiments of the above aspects or any other aspect of the invention delineated herein, the bacteria is Gram-positive or Gram-negative. In one embodiment, the bacteria is *Escherichia coli, Salmonella, Enterobacter, Klebsiella, Neisseria*, or *Pseudomonas*. In another embodiment, the bacteria is multidrug resistant *Escherichia coli*

In one embodiment, the efflux pump is a resistance nodulation cell division pump. In another embodiment, the resistance nodulation cell division pump is selected from the group consisting of AcrAB-TolC, MexAB-OprM, and MexXY-OprM.

In yet another embodiment, the antibiotic is selected from the group consisting of a fluoroquinolone, aminoglycoside, macrolide, beta-lactam, tetracycline, cephalosporins, and chloramphenicol. In another embodiment, the antibiotic is ciprofloxacin, levofloxacin, kanamycin, erythromycin, oxacillin, piperacillin, amoxicillin, or azithromycin.

In one embodiment, the method reduces the minimum inhibitory concentration of the antibiotic by at least 4-fold, 8-fold, or 16-fold. In another embodiment, the method inhibits efflux from the efflux pump by at least about 75%, 85%, 95% or more.

In another aspect, the present invention provides a pharmaceutical composition for treating a bacterial infection comprising an effective amount of 3,4-dibromopyrrole-2,5-dione in a pharmaceutically acceptable excipient. In one embodiment, the pharmaceutical composition comprises an effective amount of an antibiotic. In another embodiment, the antibiotic is selected from the group consisting of a fluoroquinolone, aminoglycoside, macrolide, beta-lactam, tetracycline, cephalosporins, and chloramphenicol. In yet another embodiment, the antibiotic is ciprofloxacin, levofloxacin, kanamycin, erythromycin, oxacillin, piperacillin, amoxicillin, or azithromycin. In one embodiment, the bacterial infection is multidrug resistant.

In yet another aspect, the present invention provides a kit for treating a bacterial infection in a subject, the kit comprising an effective amount of 3,4-dibromopyrrole-2,5-dione. In one embodiment, the kit comprises an antibiotic selected from the group consisting of a fluoroquinolone, aminoglycoside, macrolide, beta-lactam, tetracycline, cephalosporins, and chloramphenicol. In another embodiment, the antibiotic is ciprofloxacin, levofloxacin, kanamycin, erythromycin, oxacillin, piperacillin, amoxicillin, or azithromycin.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, small compound, or any other molecule. For example, the agent may be 3,4-dibromopyrrole-2,5-dione. In another embodiment, the agent is an antibiotic, such as fluoroquinolone (e.g., ciprofloxacin, levofloxacin, gemifloxacin, moxifloxacin, norfloxacin, ofloxacin), an aminoglycoside (e.g., kanamycin, gentamicin, streptomycin, neomycin, tobramycin, amikacin, paromycin), a macrolide (e.g., erythromycin, azithromycin, clarithromycin, fidaxomicin, telithromycin), a beta-lactam (e.g., oxacillin, penicillin, cloxacillin, dicloxacllin, nafcillin, amoxicillin, carbenicillin, cefadroxil, ampicillin, piperacillin), tetracycline, chloramphenicol, or any suitable molecule with antimicrobial properties to kill, reduce, prohibit, or inhibit the growth of microorganisms. The term "active agent," as used herein, refers to an agent having activity useful for treating or preventing a disease. An active agent, for example, may be 3,4-dibromopyrrole-2,5-dione. An active agent may also be an antibiotic. The terms "active agent," "therapeutic agent," "active substance," "active drug," "active ingredient," "active therapeutic substance," or "active therapeutic" are used interchangeably herein.

By "ameliorate" is meant decrease, suppress, attenuate, diminish, arrest, or stabilize the development or progression of a disease.

By "alteration" is meant a change (increase or decrease) in the expression levels (e.g., messenger RNA, micro RNA, RNA, protein) or activity of a gene, polypeptide, or other molecule as detected by standard art known methods such as those described herein. As used herein, an alteration includes a 5% change in expression levels, 10% change in expression levels, a 25% change, a 40% change, and a 50% or greater change in expression levels.

By "antibiotic" is meant an agent which reduces, prohibits, limits, or inhibits the activity of or kills a bacteria. As used herein, an antibiotic includes, but is not limited, an agent which has synergistic properties (e.g., is transported with the RND efflux pumps) with 3,4-dibromopyrrole-2,5-dione such as ciprofloxacin, levofloxacin, kanamycin, erythromycin, oxacillin, piperacillin, tetracycline, chloramphenicol, or any suitable molecule with antimicrobial properties. By "activity of an antibiotic" or "antibiotic activity" is meant the ability of an antibiotic to reduce, regress, or inhibit the growth or multiplication, or prohibit, or inhibit the activity of or kill a bacteria.

By "antibiotic resistant," "antibiotic resistant bacteria," or the like is meant to refer to bacteria capable of resisting, avoiding, expelling, enduring, or otherwise persevering through the activity of the agent (i.e., antibiotic) to continue the survival and/or proliferation of the bacteria. An antibiotic resistant bacteria is capable of resisting the activity of one or more agents (e.g., antibiotics, small molecules).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence, or amount of the analyte to be detected.

By "disease" is meant any condition or disorder that damages or interferes with the normal function of a cell, tissue, organ, organism, or system. Examples of diseases include bacterial infection or condition, including multidrug resistant bacterial infection.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "efflux pump" is meant a protein transporter localized in a membrane (e.g., cytoplasmic, nuclear, mitochondrial) of a cell. An efflux pump expels compounds or molecules from within the cell into the external environment. Efflux pumps may function via energy-dependent mechanisms. For example, an efflux pump may utilize adenosine triphosphate hydrolysis as a source of energy. An efflux pump may also function by coupling transport to an electrochemical potential difference.

As used herein, a "substrate of an efflux pump" or "efflux pump substrate" is a compound or molecule that is transported by an efflux pump. Efflux pumps may be specific for a particular substrate or may expel a broad range of substrates. For example, resistance nodulation cell division (RND) pumps recognize and expel a broad range of substrates, including antibiotics, charged and neutral molecules, organic solvents, lipids, bile salts, quorum signal molecules, and/or other molecules. A "multidrug efflux pump" extrudes a wide range of xenobiotics including drugs.

By "inhibitor of an efflux pump" or "efflux pump inhibitor" or "EPI" is meant an agent that reduces or prohibits the ability of an efflux pump to extrude substrate.

In reference to efflux inhibitors, "inhibits," or "inhibiting" is refers to reduction or interference with the normal activity of the bacteria or efflux pump.

The terms "isolated," "purified," or "biologically pure" refer to material that is free to varying degrees (e.g., at least 20%, 30%, 40%, 50%, 60%, 70%, 80%, 90%, 95%, 97%, 98%, 99%, 100% pure) from components which normally accompany it as found in its native state. "Isolate" denotes a degree of separation from original source or surroundings. An "isolate" as used herein may also denote a microbial species or microbial sample separated from its original source or surroundings.

As used herein, a "minimum inhibitory concentration (MIC)" is the lowest concentration of an antibiotic or molecule that results in no visible growth of a bacteria. The minimum inhibitory concentration may be further referred to as the amount or concentration that results in 10% inhibition of growth ($MIC_{10}$)), 50% inhibition of growth ($MIC_{50}$), 90% inhibition of growth ($MIC_{90}$) etc.

As used herein, a "multidrug resistant bacteria" is a bacteria that is resistant to multiple types of drugs, antibiotics, or other suitable molecules. An "antibiotic resistant bacteria" is a bacteria resistant to one or more antibiotics. Multidrug resistance or antibiotic resistance in bacteria may result from increased expression of efflux pumps that expel a broad range of drugs, antibiotics, or molecules. A "multidrug resistant infection" is an infection by a multidrug resistant bacteria. Multidrug resistance or antibiotic resistance in a bacteria may be reversed by inhibiting efflux pumps in the bacteria.

As used herein, "obtaining" as in "obtaining an agent" includes synthesizing, isolating, deriving, purchasing, or otherwise acquiring the agent.

By "reduces" is meant a negative alteration of at least 5%, 10%, 25%, 50%, 75%, or 100%.

By "reference" is meant a standard, control condition, or a set threshold determined by one in the art.

By "subject" is meant a mammal, including, but not limited to, a human or non-human mammal, such as a bovine, equine, canine, ovine, feline, or other suitable living being.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder (i.e. disease) and/or symptoms associated therewith. It will be appreciated that, although not precluded, treating a disorder or condition does not require that the disorder, condition, or symptoms associated therewith be completely eliminated.

Unless specifically stated or obvious from context, as used herein, the term "or" is understood to be inclusive. Unless specifically stated or obvious from context, as used herein, the terms "a," "an," and "the" are understood to be singular or plural. Unless specifically stated or obvious from context, as used herein, the term "bacteria" is understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 depicts a structure of 3,4-dibromopyrrole-2,5-dione (bottom right), an array of wells used in an example screening assay (top right), and a schematic representation of an efflux pump (left).

FIGS. 2A-2B depict data on *Pseudoalteromonas piscicida* isolates. FIG. 2A is a dendogram displaying the phylogenetic relationship of isolates within the *Pseudoalteromonas piscicida* clade. The tree was constructed with nearly full 16S rRNA gene sequences (>1400 bp) in ARB using a combination of Distance Matrix and Neighbor Joining methods and 1000 bootstraps. Nodes displaying >50% confidence are shown. The tree includes all described *P. piscicida* members in the Silva database at the time of construction (Sep. 24, 2014). FIG. 2B is a table displaying data on the 36 microbial isolates identified as *Pseudoalteromonas* species in the in-house culture collection.

FIG. 3A is a $^1$H-NMR spectrum (300 MHz, DMSO-$d_6$) of 3,4-dibromopyrrole-2,5-dione authentic standard. FIG. 3B is a $^{13}$C-NMR spectrum (75 MHz, DMSO-$d_6$) of 3,4-dibromopyrrole-2,5-dione authentic standard. FIG. 3C is a $^1$H-NMR spectrum (300 MHz, DMSO-$d_6$) of the A757 active constituent. FIG. 3D is a $^{13}$C-NMR spectrum (75 MHz, DMSO-$d_6$) of the A757 active constituent. FIG. 3E is a total compound chromatogram (TCC) of active wells. FIG. 3F is an extended ion chromatogram (EIC) of 3,4-dibromopyrrole-2,5-dione from A757 extract. FIG. 3G depicts a mass spectrum ((−)-HRESI) of the A757 active constituent and a mass spectrum of a pure 3,4-dibromopyrrole-2,5-dione standard (inset).

FIG. 4 is a table showing that 3,4-dibromopyrrole-2,5-dione potentiates the antibacterial activity of various classes of antibiotics against *E. coli* strains that overexpress efflux pumps. The antibiotics listed in FIG. 4 are chloramphenicol (CHL), ciproflaxin (CIP), erythromycin (ERY), kanamycin (KAN), levofloxacin (LEV), oxacillin (OXA), piperacillin (PIP), and tetracycline (TET). The columns labeled "MIC$^b$" list minimum inhibitory concentrations (MIC) of the antibiotic alone. The columns labeled "MIC$^c$" list minimum inhibitory concentrations (MIC) of the antibiotic in the presence of 3,4-dibromopyrrole-2,5-dione (the concentration of 3,4-dibromopyrrole-2,5-dione, in μg/ml, is shown in parentheses). The columns labeled "FICI$^d$" show fractional inhibitory concentration indices. All minimum inhibitory concentration (MIC) values are in μg/ml.

In FIG. 5A and FIG. 5B, arrows indicate time of drug addition.

FIG. 6 is a table showing Hoechst 33342 accumulation and efflux in the presence of 3,4-dibromopyrrole-2,5-dione. FIG. 6 displays final mean values from the last 4 minutes of the assay, compared using a one-way ANOVA with Dunnett's multiple comparison test comparing treatment versus Hoechst H33342 control. The level of significance is indicated by asterisks (***$p<0.0001$,*$p<0.05$, n=8). The IC$_{50}$ value calculated from efflux data was 0.79 g/mL or 3 M (95% confidence interval 0.69-0.91 g/mL). "AG100" refers to wild-type *E. coli* K-12 strain. "AG100A" refers to ΔacrAB mutant. "RFU" refers to relative fluorescent unit.

DETAILED DESCRIPTION OF THE INVENTION

Figure 1:
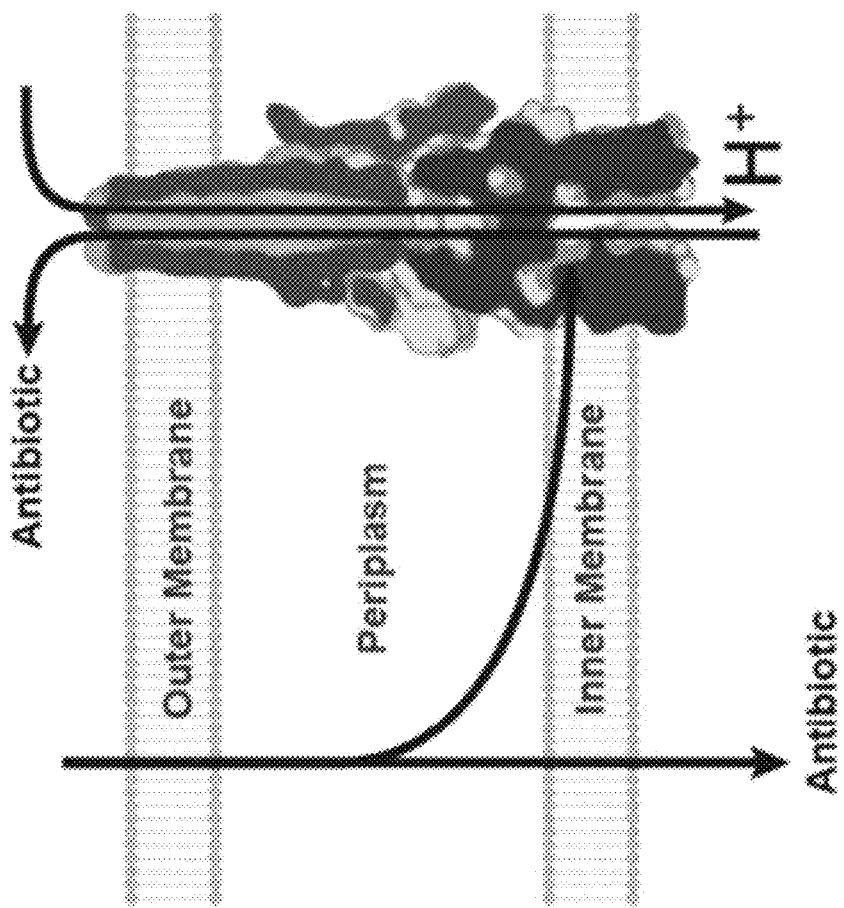
FIG. 1 is a schematic summarizing the study described herein.
Figure 1:
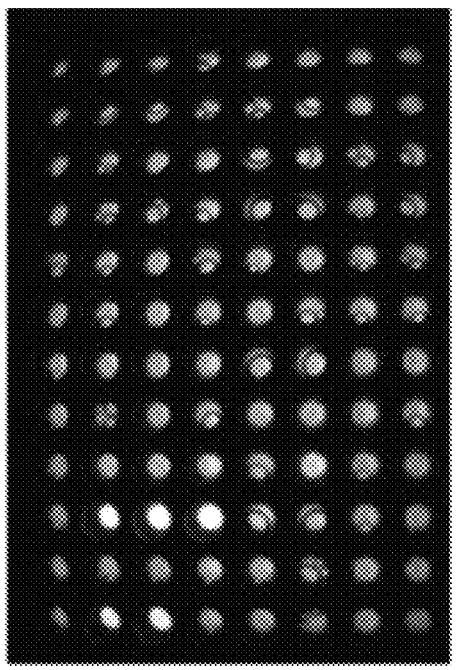
Figure 1:
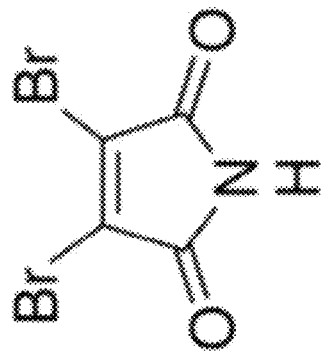

The invention features compositions and methods that are useful for increasing antibiotic activity and reducing antibiotic resistance.

The invention is based, at least in part, on the discovery that 3,4-dibromopyrrole-2,5-dione inhibits efflux pump activity in bacteria, thereby increasing the effectiveness of an antibiotic against the bacteria. Members of the resistance nodulation cell division (RND) of efflux pumps play essential roles in multidrug resistance (MDR) (e.g., resistant to 2 agents, resistant to ≥3 agents, resistant to ≥4 agents or more)

in bacteria such as Gram-negative bacteria. As reported in detail below, a search was performed for new small molecules from marine microbial extracts to block efflux and thus restore antibiotic susceptibility in MDR bacterial strains. This search resulted in the isolation of 3,4-dibromopyrrole-2,5-dione, an inhibitor of RND transporters from Enterobacteriaceae and *Pseudomonas aeruginosa*, and from the marine bacterium *Pseudoalteromonas piscicida*. 3,4-Dibromopyrrole-2,5-dione decreased the minimum inhibitory concentrations (MICs) of two fluoroquinolones, an aminoglycoside, a macrolide, a beta-lactam, tetracycline, and chloramphenicol between 2- and 16-fold in strains overexpressing three archetype RND transporters (AcrAB-TolC, MexAB-OprM, and MexXY-OprM). 3,4-Dibromopyrrole-2,5-dione also increased the intracellular accumulation of Hoechst 33342 in wild-type but not in transporter deficient strains and prevented H33342 efflux ($IC_{50}$=0.79 g/mL or 3 M), a hallmark of efflux pump inhibitor (EPI) functionality. A metabolomic survey of 36 *Pseudoalteromonas* isolates mapped the presence of primarily brominated metabolites only within the *P. piscicida* phylogenetic clade, where a majority of antibiotic activity was also observed, suggesting a link between halogenation and enhanced secondary metabolite biosynthetic potential. In sum, 3,4-dibromopyrrole-2,5-dione is a potent EPI and deserves further attention as an adjuvant to enhance the effectiveness of existing antibiotics. Accordingly, the invention features compositions comprising 3,4-dibromopyrrole-2,5-dione, alone or in combination with an antibiotic, and methods of using 3,4-dibromopyrrole-2,5-dione to enhance the antibiotic efficacy of another agent, and/or reduce the propensity of a bacteria to develop resistance to an agent.

Multidrug Resistance

The emergence of multidrug-resistant (MDR) bacterial pathogens (e.g., Gram-negative, Gram-positive), which includes Enterobacteriaceae and *Pseudomonas aeruginosa*, has become a substantial threat to treating infectious disease. Twenty percent of all deaths globally are the result of bacterial infections, and hospital-acquired infections are the sixth leading cause of mortality in the U.S., with 23,000 deaths per year due to MDR infections in the U.S. alone. The rapid decline in antibiotic effectiveness has led some clinicians to estimate the future utility of available antibiotics to be limited to a few years, in some cases, against MDR strains. Developing tools to battle these emerging MDR bacterial pathogens, particularly Gram-negative pathogens, deserves priority status, as they now account for nearly 70% of infections in intensive care units the U.S. Alarmingly, many Gram-negative clinical strains are becoming resistant to nearly all antibiotics including aminoglycosides, cephalosporins, fluoroquinolones, and carbapenems, leaving few antibiotics in the therapeutic repertoire to treat these infections. In the search for new antimicrobials, random screening of libraries of synthetic or natural products is estimated to have a primary hit rate of up to 1000-fold lower against Gram-negative than for Gram-positive bacteria. Of the antibiotics approved by the FDA from 1998 to 2005, including those in clinical trials and various stages of preclinical development, most lack appropriate activity against any Gram-negative bacteria. Making incremental improvements to the chemical scaffolds of existing antibiotics is at best a short-term strategy for the impelling need for both new drugs and novel approaches to combat multidrug-resistant pathogens. Consequently, developing compounds targeting the resistance mechanisms themselves is warranted (e.g., the clinically proven beta-lactam/beta-lactamase inhibitor cocktail, amoxicillin/clavulanic acid), thereby (i) obviating the emergence of resistance and (ii) regaining antibiotic potency.

Efflux Pumps

In some embodiments, the invention features compositions and methods of inhibiting an efflux pump in a bacterium. In other embodiments, the invention features compositions and methods of inhibiting development of antibiotic resistance or multidrug resistance in bacteria. The rapid rise of antibiotic resistance is largely a result of constitutive overexpression of transmembrane efflux pumps that expel antibiotics before they can reach their intracellular target. Members of the resistance nodulation cell division (RND) superfamily of MDR pumps have been implicated in the high intrinsic resistance of Gram-negative species, whose tripartite RND pumps recognize and expel a broad range of substrates (including antibiotics, charged and neutral molecules, organic solvents, lipids, bile salts, and quorum signal molecules), via a coupled exchange with protons or ions. Permanent overexpression of RND pumps leads to multidrug resistance in bacteria, while their deletion restores antibiotic susceptibility, further confirming this transporter is an important therapeutic target. Polyspecificity of RND pumps is central to the emergence and spreading of efflux-mediated resistance, as these pumps subsequently allow for acquisition of additional resistance mechanisms and have a significant role in bacterial pathogenicity/virulence, invasion, adherence, and host colonization. In drug-resistant *Escherichia coli, Salmonella enterica, Enterobacter aerogenes*, and *Klebsiella pneumoniae*, the AcrAB-TolC pump and its homologue MexAB-OprM/MexXYOprM in *Pseudomonas aeruginosa* are the main RND archetypes reported in clinical isolates. RND transporters are found in both prokaryotes and eukaryotes; however, homology between bacterial and human RND proteins is negligibly low (16% identity), suggesting minimal overlap in RND transporter substrate specificities. In addition, clinical isolates with more resistant MDR phenotypes (resistant to ≥5 antibiotics, including 100% fluoroquinolone resistance) are more likely to overexpress the RND pump AcrAB, suggesting this RND pump maybe a biomarker of MDR, making these efflux pumps "key" targets for the development of an efflux pump inhibitor (EPI) as an adjuvant to existing antibiotics.

Efflux Pump Inhibitors

The present invention features methods and compositions for inhibiting an efflux pump in a bacteria. The search for small-molecule efflux pump inhibitors (EPIs) from the microbial realm described herein has been aided by the fact that natural products have often been selected precisely for their ability to penetrate both outer and inner membranes of bacteria (Wright (2014), *Can. J. Microbiol.*, 60, 147-154). A countermeasure by antibiotic-producing microbes is to coevolve inhibitors of their competitor's resistance mechanisms to enhance the efficacy of their own antibiotics (Wright (2014), *Can. J. Microbiol.*, 60, 147-154), exemplified by the *Streptomyces* species producing both beta-lactam antibiotics and the beta-lactamase inhibitor clavulanic acid (Challis et al. (2003), *Proc. Natl. Acad. Sci. U.S.A.*, 100 (Suppl 2), 14555-14561). There is substantial evidence that marine bacteria produce cocktails of both antibiotics to control surface colonization (Long et al. (2003), *Appl. Environ. Microbiol.*, 568-576; Long et al. (2005) *Appl. Environ. Microbiol.*, 71, 8531-8536) and nontoxic secondary metabolites capable of quenching quorum sensing-controlled activities in other species (Teasdale et al. (2009), *Appl. Environ. Microbiol.*, 75, 567-572). However, no systematic study has screened for EPIs from marine microbial exudates (i.e., compounds excreted into the extracellular medium) against resistance nodulation cell division (RND) pumps. Regardless, the approach described herein is validated by previous screening of terrestrially derived microbial fermentations, which resulted in two new natural product EPIs targeting MexAB-OprM from *Streptomyces* (EA-371 and EA-371), potentiating levofloxacin minimum inhibitory concentrations (MICs) 4-fold and 8-fold, respectively (Stavri et al. (2007), *J. Antimicrob. Chemother.* 59, 1247-1260). The microbial EPI MP-601,205 is currently used to treat *P. aeruginosa* respiratory infections in cystic fibrosis patients (Tegos et al. (2011), *Curr. Pharm. Des.*, 17, 1291-1302). Thus far, a diverse set of natural product chemical scaffolds (including polyphenols, flavones, flavonols, flavonolignans, flavonoids, diterpenes, triterpenoids, oligosaccharideglycosides, pyridines, etc.) have been validated as EPIs in Gram-positive bacteria such as *Staphylococcus aureus* (Kourtesi et al. (2013) *Open Microbiol. J.*, 7, 34-52). A remaining challenge is the discovery of EPIs targeted toward Gram-negative efflux pumps (Kourtesi et al. (2013) *Open Microbiol. J.*, 7, 34-52).

It was hypothesized that microorganisms obtained from the marine environment produce EPIs as regulators of diverse ecological interactions and, as such, present a unique bioprospecting opportunity. In the study described herein, the objectives were to (i) screen an in-house chemical library to identify marine microbial isolates capable of reducing antibiotic MICs ≥4-fold in three strains overexpressing three archetype RND transporters (AcrAB-TolC, MexAB-OprM, and MexXY-OprM) common in Gram-negative pathogens, (ii) isolate and chemically characterize the putative EPI lead, (iii) evaluate the potential of the lead molecule to potentiate the activity of various classes of antibiotics, (iv) quantify the inhibitory activity of this molecule in functional whole cell accumulation and efflux assays, and (v) compare the exometabolomic fingerprints (i.e., the relative abundances of chemical features with unique m/z values and retention times) of EPI-producing *Pseudoalteromonas* strains with other related members of the genus, thereby linking metabolite diversity with genetic relatedness.

Described herein are the isolation, identification, and demonstration of EPI functionality of 3,4-dibromopyrrole-2,5-dione from the marine bacterium *Pseudoalteromonas piscicida*. The study described herein also demonstrates that the production of halogenated secondary metabolites is associated with those *Pseudoalteromonas* clades harboring antibiotic compounds and EPIs, further highlighting that marine microbial sources, especially marine Gram-negative bacteria, represent a tractable source of new chemical scaffolds for EPI development.

Antibiotics

The present invention features antibiotic compositions useful for inhibiting the survival and/or proliferation of a bacterium. In one embodiment, the present invention features a method of inhibiting development of antibiotic resistance in a bacterium. In another embodiment, the present invention features a method of increasing the efficacy of an antibiotic. For example, by contacting bacteria with 3,4-dibromopyrrole-2,5-dione in combination with an antibiotic, the efficacy of the antibiotic is thereby increased. In another embodiment, the present invention features a pharmaceutical composition for treating a bacterial infection comprising an effective amount of 3,4-dibromopyrrole-2,5-dione in a pharmaceutically acceptable excipient, alone or in combination with an antibiotic.

As described herein, combating a bacterial infection with an antibiotic alone may not effectively reduce the activity of, inhibit the proliferation of, or kill the bacteria, particularly if the bacteria expresses efflux pumps that extrude the antibiotic. Contacting the bacteria with 3,4-dibromopyrrole-2,5-dione in combination with an antibiotic reduces the activity of efflux pumps in the bacteria, thereby reducing extrusion of the antibiotic from the bacteria and allowing the antibiotic to reduce bacterial proliferation or survival.

Antibiotics useful in the methods and compositions of the invention are those which have synergistic properties with 3,4-dibromopyrrole-2,5-dione, including but are not limited to, those which reduce the activity of the RND transport system, but may be effective against other bacterial multidrug transporters. Most often they will act preferentially on Gram-negative organisms. Specific examples include, the beta-lactams (e.g., penicillin G, penicillin V, ampicillin, carboxypenicillin, carbenicillin, nafcillin, methicillin, oxacillin, amoxicillin, cloxacillin, dicloxacillin, and piperacillin), the mono-lactams (e.g., aztreonam), the cephalosporins (e.g., cefaclor, cefazolin, cefuroxime, cefotaxime, and ceftriaxone, ceftazidime, moxalactam), the carbapenems (e.g., imipenem, ertapenem, doripenem, and meropenem), the tetracyclines and glycylclines (e.g., doxycycline, minocycline, tetracycline, and tigecycline), the aminoglycosides (e.g., amikacin, gentamycin, kanamycin, neomycin, paromycin, streptomycin, and tobramycin), the macrolides (e.g., azithromycin, clarithromycin, fidaxomicin, telithromycin, and erythromycin), the quinolones and fluoroquinolones (e.g., gatifloxacin, moxifloxacin, sitafloxacin, ciprofloxacin, lomefloxacin, levofloxacin, gemifloxacin, ofloxacin, and norfloxacin), the glycopeptides (e.g., vancomycin, teicoplanin, dalbavancin, and oritavancin), dihydrofolate reductase inhibitors (e.g., cotrimoxazole, trimethoprim, and fusidic acid), the streptogramins (e.g., synercid), the oxazolidinones (e.g., linezolid), the lipopeptides (e.g., daptomycin), or any suitable agent with antimicrobial properties. Antibiotics useful in the methods and compositions of the invention also include, but are not limited to, lincomycins, polymyxins, sulfonamides, chloramphenicol, metronidazole, and spectinomycin.

In one embodiment, a composition of the invention comprises 3,4-dibromopyrrole-2,5-dione and a fluoroquinolone (e.g., ciprofloxacin, levofloxacin), an aminoglycoside (e.g., kanamycin), a macrolide (e.g., erythromycin, azithromycin), a beta-lactam (e.g., oxacillin, piperacillin, amoxicillin), a carbapenam (e.g., imipenem, meropenem, ertapenem, doripenem), glycylclines (e.g., doxycycline, minocycline, tigecycline), tetracycline, cephalosporins, and/or chloramphenicol. In another embodiment, a composition of the invention comprises 3,4-dibromopyrrole-2,5-dione and ciprofloxacin, 3,4-dibromopyrrole-2,5-dione and levofloxacin, 3,4-dibromopyrrole-2,5-dione and kanamycin, 3,4-dibromopyrrole-2,5-dione and erythromycin, 3,4-dibromopyrrole-2,5-dione and oxacillin, 3,4-dibromopyrrole-2,5-dione and piperacillin, 3,4-dibromopyrrole-2,5-dione and tetracycline, or 3,4-dibromopyrrole-2,5-dione and chloramphenicol.

Bacteria

The present invention features methods and compositions to inhibit proliferation of bacteria. In some embodiments, the present invention provides methods of inhibiting development of antibiotic resistance in bacteria. In other embodiments, the present invention features a pharmaceutical composition for treating a bacterial infection. The present invention is expected to be useful against bacterial pathogens, and against Gram-negative organisms in particular. Exemplary Gram-negative bacterial pathogens include, but are not limited to, *Aerobacter, Aeromonas, Acinetobacter, Agrobacterium, Bacteroides, Bartonella, Bordetella, Bordetella, Borrelia, Brucella, Burkholderia, Calymmatobacterium, Campylobacter, Citrobacter, Chlamydia, Chlamydophila, Enterobacter, Enterobacter aerogenes, Escherichia, Francisella, Fusobacterium, Fusobacterium nucleatum, Gardnerella, Haemophilus, Hafnia, Helicobacter, Klebsiella, Klebsiella pneumoniae, Legionella, Leptospira, Morganella, Moraxella, Neisseria, Pasteurella, Pasteurella multocida, Plesiomonas, Prevotella, Proteus, Providencia, Pseudomonas, Porphyromonas, Rickettsia, Salmonella, Serratia, Shigella, Stentorophomonas, Streptobacillus, Streptobacillus moniliformis, Treponema, Treponema pallidium, Treponema pertenue, Xanthomonas, Veillonella, Vibrio,* and *Yersinia.*

The methods and compositions of the present invention are expected to be useful against Gram-negative and in some cases Gram-positive bacteria but most specifically, those organisms expressing the RND system. Gram-positive bacteria include, but are not limited to, *Actinomyces israelli, Bacillus* species, *Bacillus antracis, Clostridium, Clostridium perfringens, Clostridium tetani, Cornyebacterium, Corynebacterium diphtheriae, Enterococcus, Erysipelothrix rhusiopathiae, Lactobacillus, Listeria, Mycobacterium, Staphylococcus,* and *Streptococcus.*

Specific examples of infectious bacteria include but are not limited to, *Acinetobacter baumanii, Helicobacter pyloris, Borelia burgdorferi, Legionella pneumophilia,* Mycobacteria sps (e.g., *M. tuberculosis, M. avium, M. intracellulare, M. kansaii, M. gordonae), Neisseria gonorrhoeae, Neisseria meningitidis, pathogenic Campylobacter* sp., *Haemophilus influenzae, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia,* and *Actinomyces israelli*. In a one embodiment of the invention, the bacteria is Gram-negative. In other embodiments, the bacteria is *Escherichia coli, Salmonella enterica, Enterobacter aerogenes, Klebsiella pneumoniae, Neisseria gonorrhoeae,* or *Pseudomonas aeruginosa.*

Therapeutic Methods 3,4-Dibromopyrrole-2,5-dione was identified as an agent useful for preventing or ameliorating a disease associated with a bacterial infection, particularly multidrug resistant or antibiotic resistant bacterial infections. Diseases and disorders associated with bacteria, particularly those characterized by resistance to antibiotics, may be treated using the methods and compositions of the invention.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of an antibiotic composition of the invention (e.g., 3,4-dibromopyrrole-2,5-dione and one or more of an antibiotic such as fluoroquinolone (e.g., ciprofloxacin, levofloxacin), an aminoglycoside (e.g., kanamycin), a macrolide (e.g., erythromycin), a beta-lactam (e.g., oxacillin, piperacillin), tetracycline, and/or chloramphenicol) to a subject (e.g., animal, human) in need thereof, including a mammal, particularly a human. Such treatment will be suitably administered to subjects, particularly humans, suffering from, having, susceptible to, or at risk for a bacterial infection or symptom thereof. Determination of those subjects "at risk" can be made by any objective or subjective determination by a diagnostic test or opinion of a subject or health care provider (e.g., genetic test, enzyme or protein marker, family history, and the like). The antibiotic compositions herein may be also used in the treatment of any other disorders in which bacterial infection may be implicated.

Pharmaceutical Therapeutics

The invention provides methods of inhibiting the survival or proliferation of bacteria. The invention also provides methods of increasing the efficacy of an antibiotic and compositions for treating a bacterial infection. The methods and compositions of the invention comprise 3,4-dibromopyrrole-2,5-dione, and in some embodiments further comprise an antibiotic (e.g., a fluoroquinolone (e.g., ciprofloxacin, levofloxacin), an aminoglycoside (e.g., kanamycin), a macrolide (e.g., erythromycin, azithromycin), a beta-lactam (e.g., oxacillin, piperacillin, amoxicillin), tetracycline, chloramphenicol, or any suitable antibiotic or molecule). Such methods are useful for treating diseases associated with a bacterial infection, particularly multidrug resistant or antibiotic resistant bacterial infection.

For therapeutic uses, the antibiotic compositions (e.g., 3,4-dibromopyrrole-2,5-dione, alone or in combination with a fluoroquinolone (e.g., ciprofloxacin, levofloxacin), an aminoglycoside (e.g, kanamycin), a macrolide (e.g., erythromycin), a beta-lactam (e.g., oxacillin, piperacillin), tetracycline, chloramphenicol, or any suitable antibiotic or molecule) disclosed herein may be administered systemically, for example, formulated in a pharmaceutically-acceptable buffer such as physiological saline. Routes of administration include, for example, subcutaneous, intravenous, interperitoneally, intramuscular, intradermal injections that provide continuous, sustained levels of the drug in the patient, or any appropriate method of providing the antibiotic composition to the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the bacterial infection. Generally, amounts will be in the range of those used for other agents used in the treatment of other diseases associated with bacterial infection, although in certain instances lower amounts will be needed because of the increased specificity of the compound. An antibiotic is administered at a dosage that reduces proliferation, survival, activity of, or kills bacteria as determined by a method known to one skilled in the art, or using any that assay that measures activity of the antibiotic against the bacteria (for example, the minimum inhibitory concentration of an antibiotic). In one embodiment, 3,4-dibromopyrrole-2,5-dione is administered at a dosage that increases activity of a conventional antibiotic against the bacteria or reduces the propensity of the bacteria to develop resistance against the antibiotic. In one embodiment, 3,4-dibromopyrrole-2,5-dione is administered at a dosage that reduces the minimum inhibitory concentration of the antibiotic by at least 2- or 4-fold (e.g., 2-, 3-, 4-, 5-, 6-, 7-, 8-, 9-, 10-fold or more). In particular embodiments, 3,4-dibromopyrrole-2,5-dione is administered prior to administration of the antibiotic, concurrently with the antibiotic, or following administration of the antibiotic. In one embodiment, 3,4-dibromopyrrole-2,5-dione is administered with one or more agents or antibiotics.

Formulation of Pharmaceutical Compositions

The administration of 3,4-dibromopyrrole-2,5-dione (alone or in combination with an agent(s)) for the treatment of a bacterial infection may be by any suitable means that results in a concentration of the therapeutic that, combined with other components, is effective in ameliorating, reducing, or stabilizing a bacterial infection. The therapeutic agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent or agents substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with tissue infected with bacteria; (v) formulations that allow for convenient dosing, such that doses are administered, for example, once every one or two weeks; and (vi) formulations that target bacteria by using carriers or chemical derivatives to deliver the therapeutic agent to a particular site or sites infected by bacteria. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added. The composition may be in the form of a solution (e.g., syrup, electuary, beverage, mouthwash, eye drops, ear drops, enema, Murphy drip, spray, alcohol, oil), a suspension (e.g., gel, hydrogel, ointment, paste, chewing gum, lozenge, suppository), an emulsion, an infusion device, or a delivery device for implantation (e.g., intrauterine device, skin tag), a dermal application (e.g., topical cream, liniments, film, patch, lotion, balm, shampoo), or any appropriate method known in the art. It may be presented as a dry powder (e.g., effervescent powder) to be reconstituted with water or another suitable vehicle before use (e.g., inhaler, vaporizer). Apart from the active agent(s) that reduces or ameliorates a bacterial infection, the composition may include suitable parenterally acceptable carriers and/or excipients. The active therapeutic agent(s) may be incorporated into microspheres, microcapsules, nanoparticles, liposomes, acrylics, or the like for controlled release. Furthermore, the composition may include suspending, solubilizing, stabilizing, pH-adjusting agents, tonicity adjusting agents, and/or dispersing, agents. In compositions suitable for dermal application, the active therapeutic agent(s) may be incorporated with petroleum jelly, beeswax, paraffin, polyethylene glycol, gelatin, or the like.

As indicated above, the pharmaceutical compositions according to the invention may be in the form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide, salt solution, 1,3-butanediol, Ringer's solution, isotonic sodium chloride solution, dextrose solution, or a suitable buffer. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added (e.g., dimethylsulfoxide, Tween, ethanol, sodium taurocolate), or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Encyclopedia of Pharmaceutical Technology, supra.

At least one antibiotic therapeutic and 3,4-dibromopyrrole-2,5-dione may be mixed together in the tablet, or may be partitioned. In one example, the antibiotic is contained on the inside of the tablet, and 3,4-dibromopyrrole-2,5-dione is on the outside, such that a substantial portion of 3,4-dibromopyrrole-2,5-dione is released prior to the release of the antibiotic.

Formulations for oral use may also be presented as chewable tablets, or as hard gelatin capsules wherein the active ingredient is mixed with an inert solid diluent (e.g., potato starch, lactose, microstalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Combination Therapies

In some embodiments, 3,4-dibromopyrrole-2,5-dione may be administered in combination with any other standard antibiotic therapy (e.g., a fluoroquinolone (e.g., ciprofloxacin, levofloxacin), an aminoglycoside (e.g., kanamycin), a macrolide (e.g., erythromycin), a beta-lactam (e.g., oxacillin, piperacillin), tetracycline, chloramphenicol and/or suitable agent); such methods are known to the skilled artisan and described in Remington's Pharmaceutical Sciences by E. W. Martin. Optionally, 3,4-dibromopyrrole-2,5-dione may be administered in combination with any other efflux pump inhibitor. The combination of 3,4-dibromopyrrole-2,5-dione with other efflux pump inhibitor(s) may also be administered in combination with an antibiotic or other standard antibiotic therapy. In one embodiment, a combination of 3,4-dibromopyrrole-2,5-dione and an antibiotic includes concurrent administration. In another embodiment, the 3,4-dibromopyrrole-2,5-dione is administered less than about 1, 2, 3, 4, 5, or 6 hours before or after the antibiotic. In another embodiment, the 3,4-dibromopyrrole-2,5-dione is administered within about 8, 10, 12, 20, 24 hours or more of the antibiotic.

Kits

The invention provides kits for the treatment or prevention of bacterial infection, particularly multidrug resistant or antibiotic resistant bacterial infection. In one embodiment, the kit includes a therapeutic or prophylactic composition containing an effective amount of 3,4-dibromopyrrole-2,5-dione in unit dosage form. In some embodiments, the therapeutic or prophylactic composition additionally contains a conventional antibiotic or other agent (e.g., a fluoroquinolone (e.g., ciprofloxacin, levofloxacin), an aminoglycoside (e.g., kanamycin), a macrolide (e.g., erythromycin), a beta-lactam (e.g., oxacillin, piperacillin), tetracycline, and/or chloramphenicol). In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired the therapeutic composition of the invention is provided together with instructions for administering the composition to a subject having or at risk of developing a bacterial infection. The instructions will generally include information about the use of the composition for the treatment or prevention of bacterial infection. In other embodiments, the instructions include at least one of the following: description of the therapeutic agent(s); dosage schedule and administration for treatment or prevention of bacterial infection or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Additional Methods

The invention may also be used in laboratory methods such as a diagnostic, an inhibitor, and other non-clinical applications. A person of ordinary skill in the art would be capable in determining suitable assay techniques, analyzing results from those assay, or establishing other parameters associated with the assay (e.g., suitable doses, administration, controls). In some embodiments, 3,4-dibromopyrrole-2,5-dione is used as a laboratory inhibitor of the RND efflux pump to investigate downstream or other effects of RND efflux pump inhibition. In other embodiments, 3,4-dibromopyrrole-2,5-dione is used in a diagnostic assay (e.g., for identifying a test subject or bacteria, as a diagnostic marker or agent, as a outcome predictor). In another embodiment, 3,4-dibromopyrrole-2,5-dione is used in a synthesis reaction. In some embodiments, 3,4-dibromopyrrole-2,5-dione is used in an assay for specificity, susceptibility, efficacy, potency, toxicity, safety, etc. of an antibiotic on a bacteria (e.g., Gram-negative), in a subject (e.g., human, mammal), in a reaction, or the like in vivo or in vitro.

The practice of the present invention employs, unless otherwise indicated, conventional techniques of molecular biology (including recombinant techniques), microbiology, cell biology, biochemistry, and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology;" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the methods and production of the therapeutic agents of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 2A:
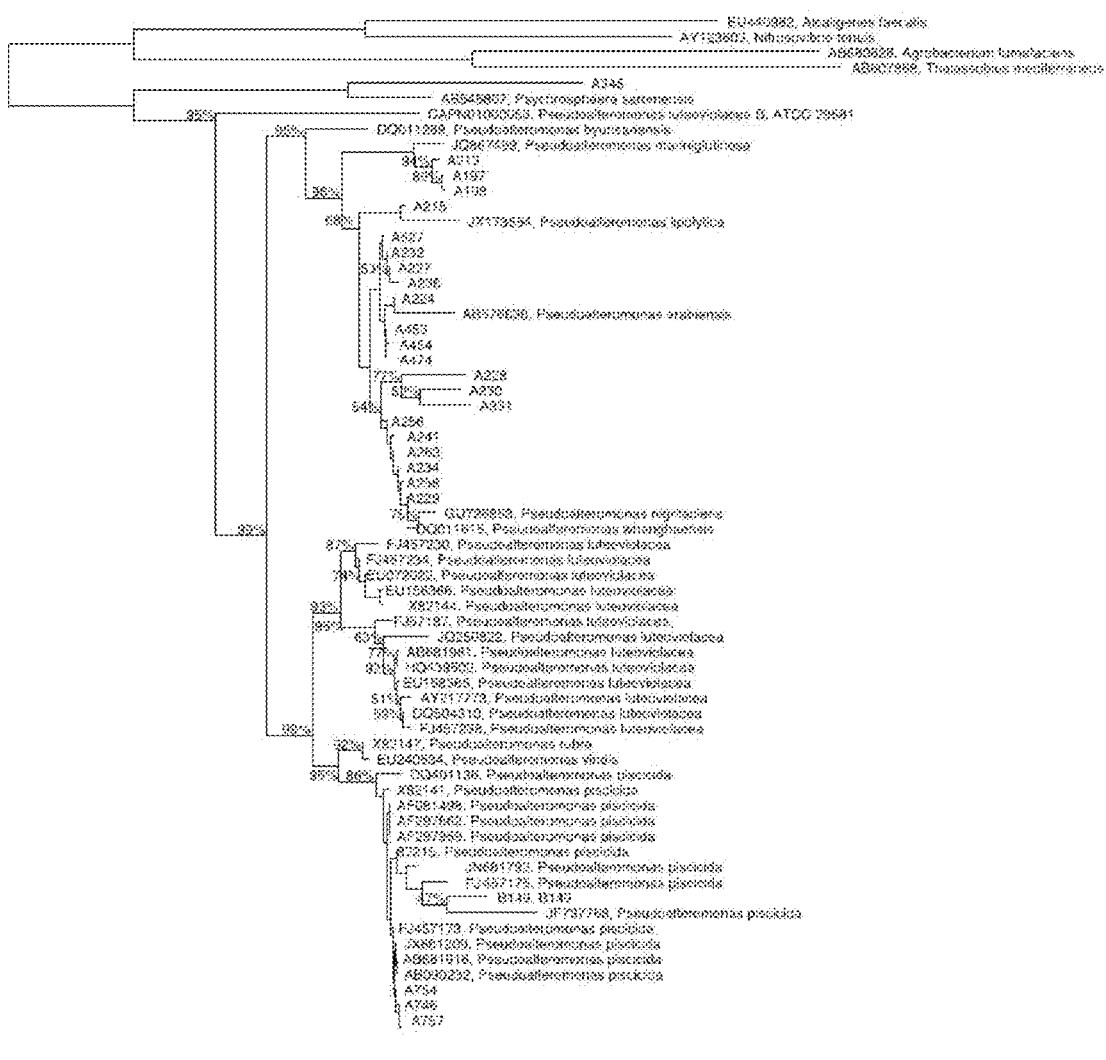
Figure 2B:
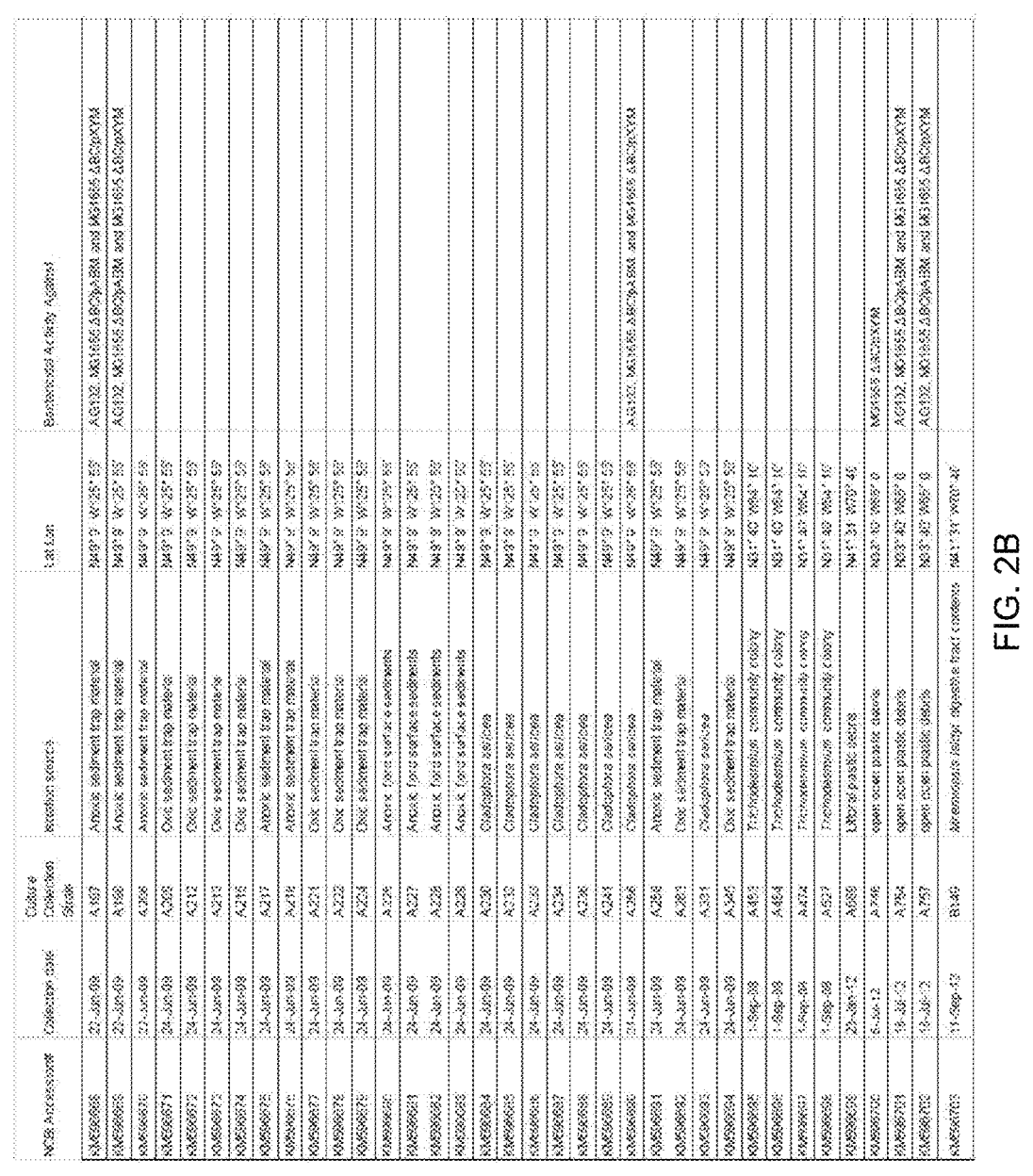

Example 1: Isolation and Identification of 3,4-Dibromopyrrole-2,5-dione as a Potentiator of Antibiotic Activity From a screen of exudate extracts of marine microbial isolates, an extract containing 3,4-dibromopyrrole-2,5-dione was identified as a potentiator of antibiotic activity (FIG. 1). Exudate extracts from a total of 1308 marine microbial isolates were screened in the p-iodonitrotetrazolium chloride (INT) assay to assess multidrug resistance reversal potential. This initial screening identified 36 marine microbial isolates of diverse phylogenetic affiliation (2.8% hit rate) capable of potentiating (i.e., reducing the antibiotic minimum inhibitory concentration (MIC) by at least 4-fold) the activity of chloramphenicol and/or erythromycin when tested against E. coli multidrug resistant (MDR) strains AG102, MG1655 ΔBC/pABM, and MG1655 ΔBC/pXYM. Phylogenetic analysis of 16S rRNA gene sequences indicated seven isolates of these 36 were Pseudoalteromonas species (A197, A198, A256, A746, A754, A757, B126) (FIGS. 2A-2B). Isolate B126 could not be revived from frozen culture; therefore, it was dropped from further analysis. Extracts displaying an initial positive hit in one or more test E. coli strains in the bacterial susceptibility assay were tested again in the presence and absence of antibiotic via the INT assay to establish the MIC of the extract (tested in a serial dilution series) and determine if efflux pump inhibitor (EPI)-like activity was present by examining the minimal effective concentration of the extract required to potentiate the antibiotic MIC at least 4-fold. These experiments indicated isolates A197, A198, and A256 produced antibiotics only, while A746, A754, and A757 demonstrated EPI potential and antibiotic activity. The strongest EPI-like activity was seen for A757; therefore, this isolate was chosen for further study. Bioassay-guided fractionation of the extract generated from 16.5 L of A757 exudates resulted in the isolation of 3,4-dibromopyrrole-2,5-dione. The structure of 3,4-dibromopyrrole-2,5-dione was established on the basis of nuclear magnetic resonance (NMR) spectroscopic and liquid chromatography-mass spectrometry (LC-MS) data in comparison with an authentic standard (FIGS. 3A-3G). This represents the first description of 3,4-dibromopyrrole-2,5-dione from a microbial source, although the original report of its isolation from nature was from the marine sponge Axinella brevistyla collected in western Japan, where it was reported to exert modest antifungal activity and cytotoxicity against murine lymphocytic leukemia cells (Tsukamoto et al. (2001), J. Nat. Prod., 64, 1576-1578). However, because over 50% of a sponge's biomass can be attributed to microorganisms, it is conceivable that the origin of 3,4- dibromopyrrole-2,5-dione may be from sponge-associated microorganisms (Still et al. (2014), J. Nat. Prod., 77, 690-702).

Example 2: 3,4-Dibromopyrrole-2,5-dione Has Antibiotic Potentiation Activity

Figure 4:
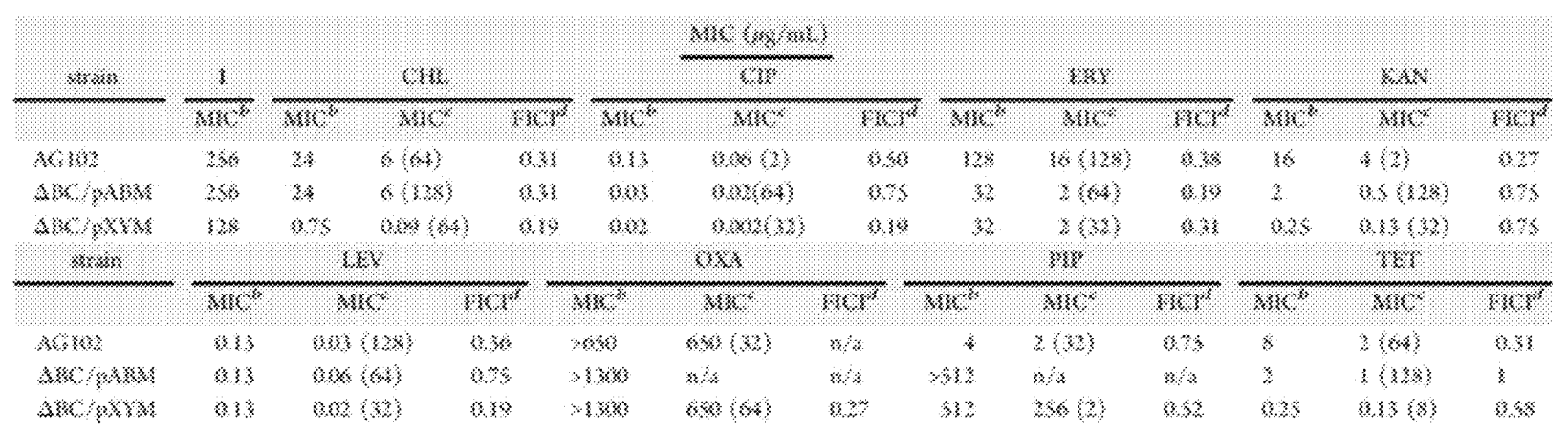

Based on assays performed, it was determined that 3,4-dibromopyrrole-2,5-dione potentiated activity of antibiotics. Moreover, it was determined that 3,4-dibromopyrrole-2,5-dione potentiated antibiotic activity by inhibiting efflux. The checkerboard assay was used to determine whether 3,4-dibromopyrrole-2,5-dione potentiates the activity of two fluoroquinolones (ciprofloxacin (CIP) and levofloxacin (LEV)), an aminoglycoside (kanamycin (KAN)), a macrolide (erythromycin (ERY)), two β-lactams (oxacillin (OXA) and piperacillin (PIP)), tetracycline (TET), and chloramphenicol (CHL), known substrates for resistance nodulation cell division pump (RND) transporters, against test strains of multidrug resistant (MDR) $E.\ coli$. Interactions between 3,4-dibromopyrrole-2,5-dione and various antibiotics were classified based upon the fractional inhibitory concentration index (FICI), where a FIC of <0.5 is synergistic and indicative of the presence of an efflux pump inhibitor (EPI); 0.5-1 is indifferent; and >1 is antagonistic. As shown in FIG. 4, 3,4-dibromopyrrole-2,5-dione decreased the minimum inhibitory concentrations (MICs) of various antibiotic classes between 2- and 16-fold, with corresponding FICIs indicating synergistic activity of 3,4-dibromopyrrole-2,5-dione with all antibiotics tested with the exception of piperacillin. 3,4-Dibromopyrrole-2,5-dione exhibited antibacterial activity at concentrations of >100 µg/mL for all three $E.\ coli$ strains overexpressing efflux pumps. The greatest decrease in antibiotic MICs was seen for erythromycin, where 3,4-dibromopyrrole-2,5-dione decreased the antibiotic MICs between 8- and 16-fold.

Figure 5A:
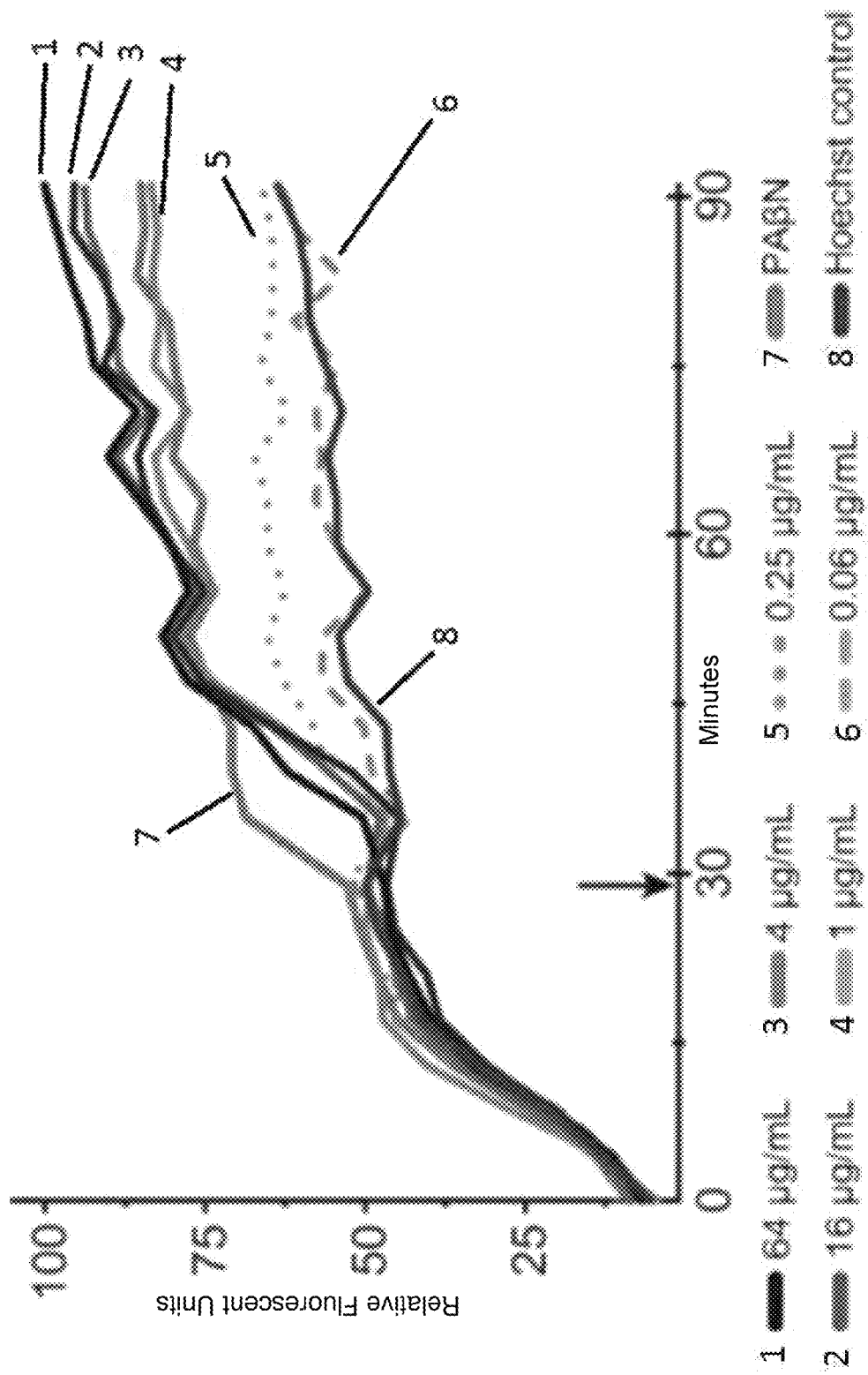
FIGS. 5A-5C are graphs depicting the effect of 3,4-dibromopyrrole-2,5-dione on Hoechst 33342 accumulation and efflux in wild-type (AG100) and transporter-deficient (AG100A) *E. coli*. Hoechst 33342 accumulation in AG100 (FIG. 5A) or AG100A (FIG. 5B) and efflux in AG100 (C) in the presence of a dilution series of 3,4-dibromopyrrole-2,5-dione. PAβN (15.6 g/mL or 28 M) was used as a positive control.
Figure 5B:
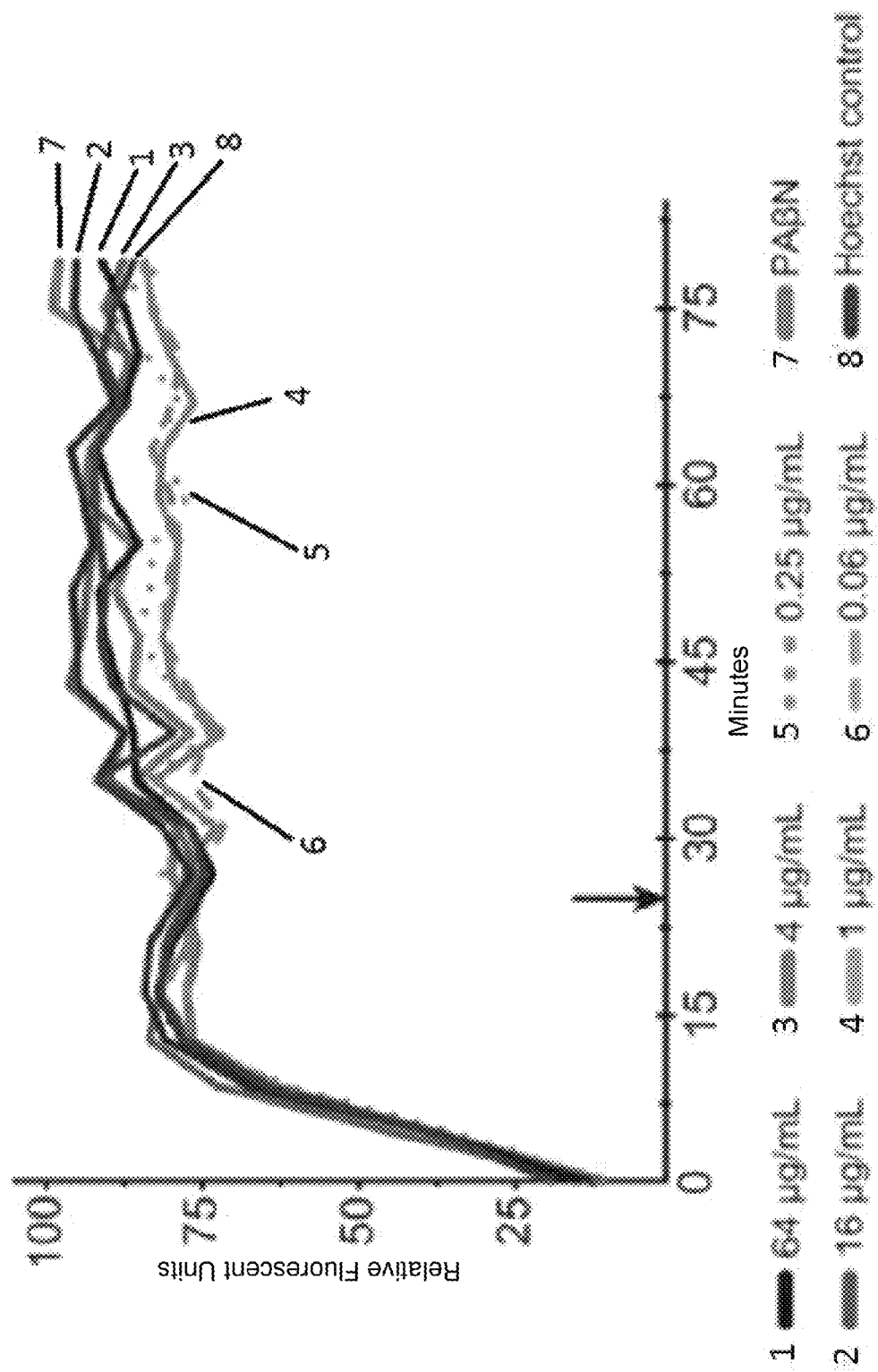

To verify that inhibition of efflux, and not membrane permeabilization, was the mechanism by which 3,4-dibromopyrrole-2,5-dione potentiated antibacterial activity, experiments were performed to determine whether 3,4-dibromopyrrole-2,5-dione was capable of causing the accumulation of the fluorescent efflux pump substrate (Hoechst 33342) in the wild-type $E.\ coli$ AG100 expressing the AcrAB-TolC pump and conversely confirm the $E.\ coli$ mutant AG100A, lacking the pump, would not be affected. Upon entering the bacterial cell, H33342 becomes fluorescent once bound to the DNA minor groove. As shown in FIG. 5A, addition of 3,4-dibromopyrrole-2,5-dione at concentrations ranging from 0.06 to 64 µg/mL resulted in a dose-dependent increase in intracellular H33342 fluorescence, consistent with an EPI effect. Concentrations of 3,4-dibromopyrrole-2,5-dione of ≥1 µg/mL were equal to or more effective than the reference inhibitor phenylalanyl arginyl β-naphthylamide (PAβN) (15.6 µg/mL) in causing H33342 accumulation. It was hypothesized that antibiotic-sensitive mutant $E.\ coli$ (AG100A), lacking the target RND pump of 3,4-dibromopyrrole-2,5-dione, would not be affected by the compound. Results displayed in FIG. 5B show no effect of 3,4-dibromopyrrole-2,5-dione on H33342 fluorescence in AG100A, consistent with the hypothesis that RND pumps are the target of 3,4-dibromopyrrole-2,5-dione and indicates multidrug resistance (MDR) reversal is limited to efflux pump expressing $E.\ coli$ strains. In addition, if the mechanism of action of 3,4-dibromopyrrole-2,5-dione was via membrane permeabilization, a dose-dependent increase in H33342 accumulation regardless of test bacterial strain would have been seen, which was not observed.

Figure 5C:
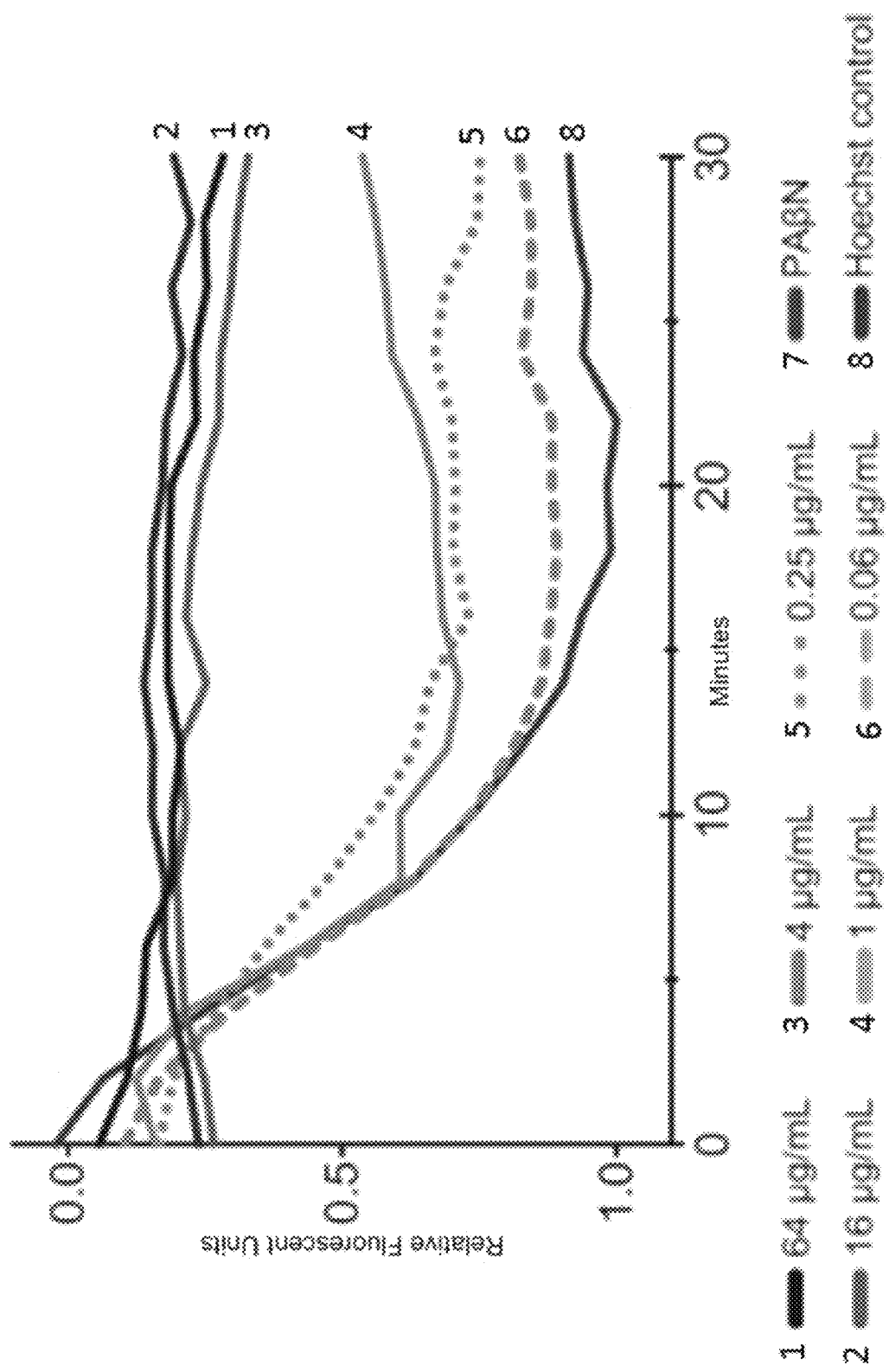

Demonstration of efflux activity in AG100 requires that accumulation of H33342 has taken place. Following H33342 "loading", monitoring of efflux was initiated in the presence of increasing concentrations of 3,4-dibromopyrrole-2,5-dione (0.06-64 µg/mL) in medium containing glucose at 37° C. The near-complete inhibition of H33342 efflux was observed in comparison to control wells (FIG. 5C), indicating efflux-competent bacterial cells were not capable of transporting H33342 in the presence of 3,4-dibromopyrrole-2,5-dione. Concentrations of 3,4-dibromopyrrole-2,5-dione as dilute as 0.06 µg/mL showed significant ($p<0.05$) H33342 efflux inhibition in comparison to solvent controls (FIG. 6). The $IC_{50}$ value for 3,4-dibromopyrrole-2,5-dione in the efflux assay was calculated to be 0.79 µg/mL or 3 µM. A comparison of bacterial RND pump EPIs revealed that the compounds, including 3,4-dibromopyrrole-2,5-dione, contained hydrophobic ring systems that presumably interact with hydrophobic residues located near or in the substrate-binding site (Opperman et al. (2014), Antimicrob. Agents Chemother. 58, 722-733).

3,4-Dibromopyrrole-2,5-dione also is known to react with thiols in the presence of a strong reducing agent such as tris(2-carboxyethyl)phosphine (Schumacher et al. (2011), Bioconjugate Chem. 22, 132-136). Without intending to be bound by theory, it is conceivable, but unlikely, that 3,4-dibromopyrrole-2,5-dione is displacing and coordinating certain accessible thiols in the RND pumps and permanently modifying their conformation by this cross-linking-type displacement; however, the lack of antibiotic activity and range of pharmacokinetics argue against this type of action. Although the subject of another study, experiments employing halogenated and nonhalogenated maleimides will be informative in terms of mode of action.

Example 3: Chemophylogenetic Analysis of Extracts from Pseudoalteromonas Isolates Analysis of the untargeted (−)-HRESI (high resolution electrospray ionization mass spectrometry) metabolomics comparison indicated the presence of many halogenated features, the distributions of which differed greatly across Pseudoalteromonas clades. Principle component analysis (PCA) of (−)-HRESI mode data (n=1112 chemical features present in Pseudoalteromonas samples at concentrations 10× those in the media-only blank) revealed that most Pseudoalteromonas clades were chemically similar overall with the exception of two clades, IV and VI, which were distinguishable from the other clades based on the first two principal components of a four-component model (capturing >60% of the total variance). Of the two clades distinguishable via PCA, clade IV contained the efflux pump inhibitor (EPI) producing strain A757 and two additional strains with EPI activity based on dilution series testing (A746 and A754), while clade VI contained two strains (A197 and A198) with antibacterial activity only (FIG. 2B). In summary, the PCA analysis of (−)-HRESI data revealed those strains with the most disparate chemistry (designated by clades IV and VI) corresponded to the majority of strains with antibiotic activity against multidrug resistant (MDR) $E.\ coli$.

In order to discern which chemical features were unique to clade IV (and subsequently strain A757), chemical feature loadings on the first principal component were examined. It is important to note that great care must be taken to avoid the assumption that any of these features alone would be significantly differentially produced by Pseudoalteromonas strains; however, examining the loadings was still useful and was likely to reveal suites of compounds with varying concentrations in different *Pseudoalteromonas* extracts. Of the 1112 features, 221 chemical features had small negative loadings (<−0.02) within the first principal component and highly positive loadings (>0.02) on the second principal component and were therefore likely candidates to distinguish clade IV from the remaining clades. Further analysis of these 221 features indicated that (i) several shared retention times and (ii) they had masses ~2 amu apart, suggesting that many chemical features represented halogenated isotopes. It was determined that, of these 221 features, 129 were isotopes of 46 individual brominated metabolites based upon both isotopic distribution and shared retention time.

Of the 46 halogenated metabolites found, all were exclusively produced by members of clade IV, demonstrating a distinct *Pseudoalteromonas* chemotype characterized by halogenation of the exometabolome. Moreover, this "halogenome" appeared to be dominated by brominated metabolites, with only some metabolites (<10) that were additionally chlorinated. In addition, several other brominated compounds (~30-40) were observed based upon isotopic signatures produced by A757 that were not accounted for in the initial 221 chemical features (screened based on their loadings), suggesting that a large percentage of the A757 exometabolome may be subject to halogenation. Relative concentrations of halogenated compounds from clade IV appeared different even within members of the same species, indicative of intraspecies chemical diversity and further subclustering among isolates of the same species (A757, A754, A746, and B149), a phenomenon previously described for *P. luteoviolacea* strains. Taken together, these results indicate that the production of halogenated compounds could be a biomarker for marine isolates with enhanced biosynthetic potential. Of the four strains in the culture collection designated as belonging to clade IV, A757 and A754 produced all 46 metabolites, whereas strains A746 and B149 produced only select halogenated metabolites, including 2,3,4,5-tetrabromopyrrole, a known weak antibiotic from *Pseudoalteromonas* species. 2,3,4,5-Tetrabromopyrrole appeared to be the most abundant brominated compound observed (retention time 20.8 min, major ion m/z 381.6722) and was present in all members of clade IV. Because of the dominance of 2,3,4,5-tetrabromopyrrole in the samples and its shared carbon skeleton with 3,4-dibromopyrrole-2,5-dione, an authentic standard of 2,3,4,5-tetrabromopyrrole was tested in efflux pump inhibitor (EPI) functionality assays and 2,3,4,5-tetrabromopyrrole was determined not to be responsible for the EPI activity of strain A757. The presence of 2,3,4-tribromopyrrole was also determined (retention time 20.1 min, major ion m/z 301.7639), which was present in A757, A754, and A746, but not in B149. 2,3,4-Tribromopyrrole was reported to be produced by *P. luteoviolacea*, found within clade IV, and is a known feeding deterrent in marine systems.

The limit of detection of 3,4-dibromopyrrole-2,5-dione with an authentic standard was established to be 11.1 ng/mL. The yield obtained from 16.5 L of A757 culture was on the order of 1 mg/L of 3,4-dibromopyrrole-2,5-dione. 3,4-Dibromopyrrole-2,5-dione should have been detected in the extract that was initially screened for antibiotic activity; however, this ion was not detected until culture scale-up and further purification, suggesting ionization masking effects from the presence of a complex mixture including 2,3,4,5-tetrabromopyrrole, which was observed to coelute with 3,4-dibromopyrrole-2,5-dione under these chromatographic conditions. In addition to numerous halogenated metabolites, other unique metabolites produced by members of clade IV (versus other *Pseudoalteromonas* clades) were also observed, when using PCA to compare metabolomes generated with (+)-HRESI data (n=1552 chemical features). However, to avoid over-interpretation of these data, a follow up with a complete characterization of these chemical features was not performed. Strain A746 was distinguished by a group of 177 chemical features, whereas other members of clade IV (strains A575, A574, B149) were more easily distinguished by a group of 56 chemical features. Although full annotation of chemical features detected in (+)-HRESI was not sought, these data also indicated (along with (−)-HRESI results) that members of clade IV possessed a characteristic exometabolome.

Figure 3A:
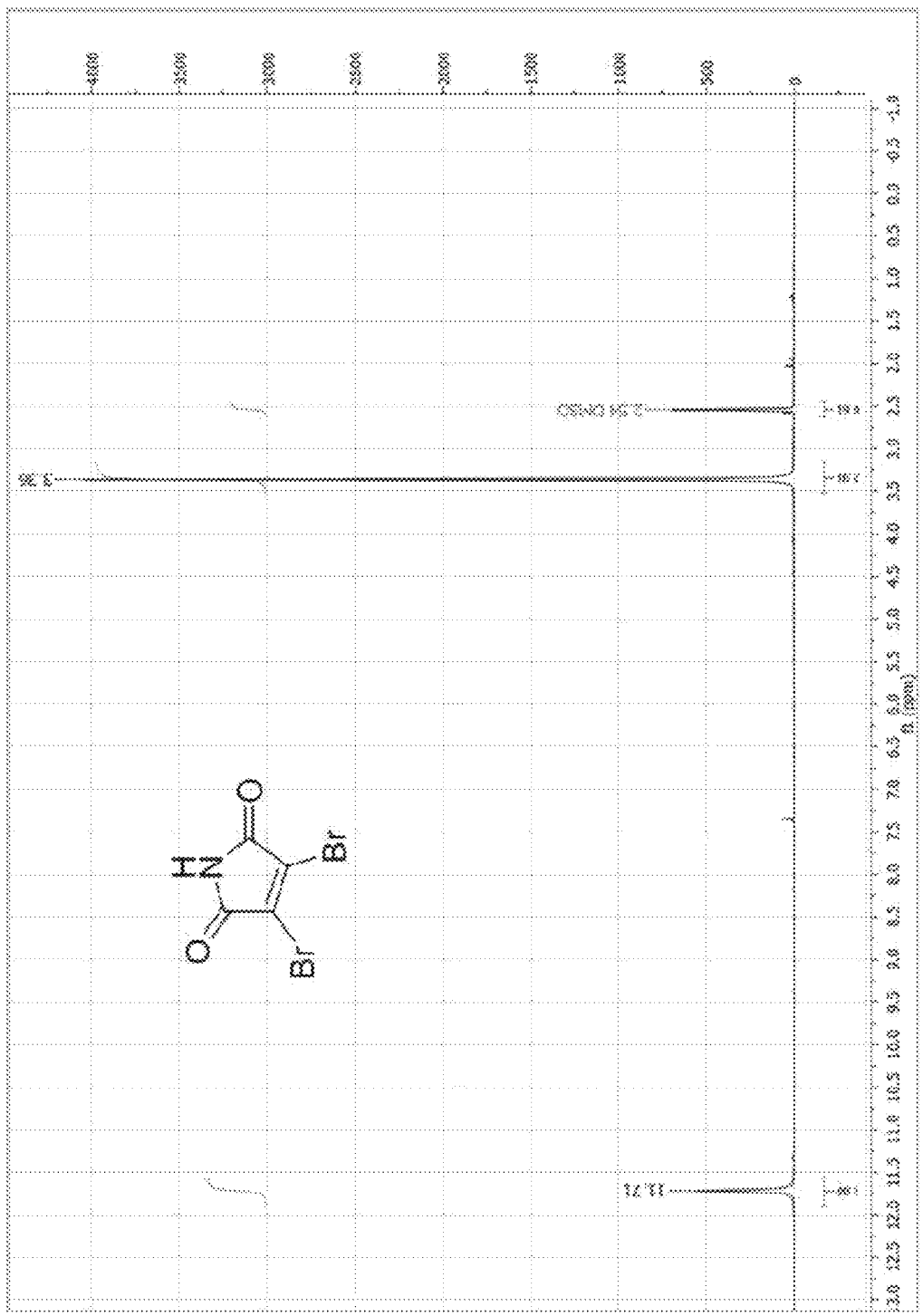
FIGS. 3A-3G are spectra from nuclear magnetic resonance (NMR) and liquid chromatography-mass spectrometry (LC-MS) analyses to identify the active constituent in the *Pseudoalteromonas* isolate A757.
Figure 3B:
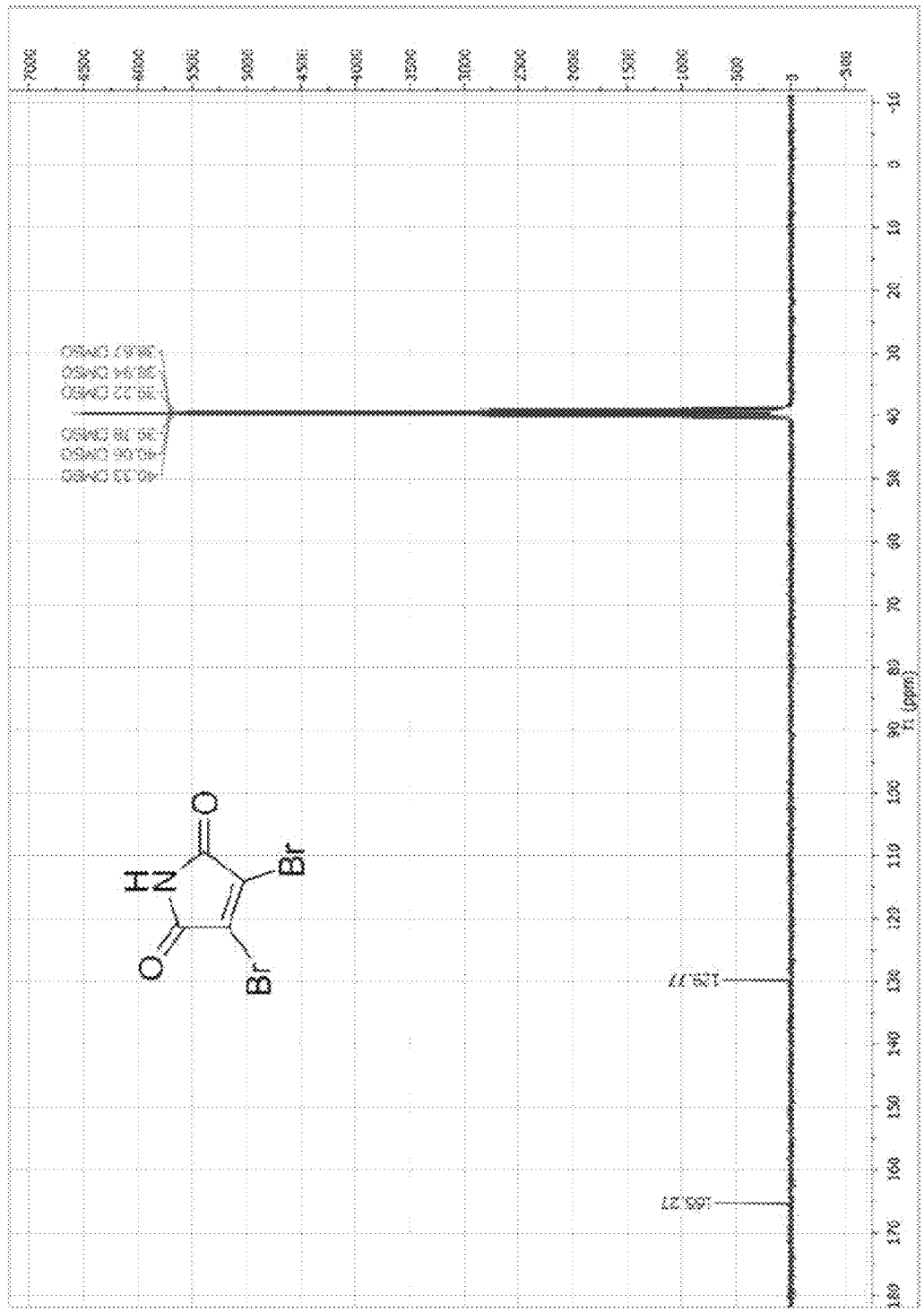
Figure 3C:
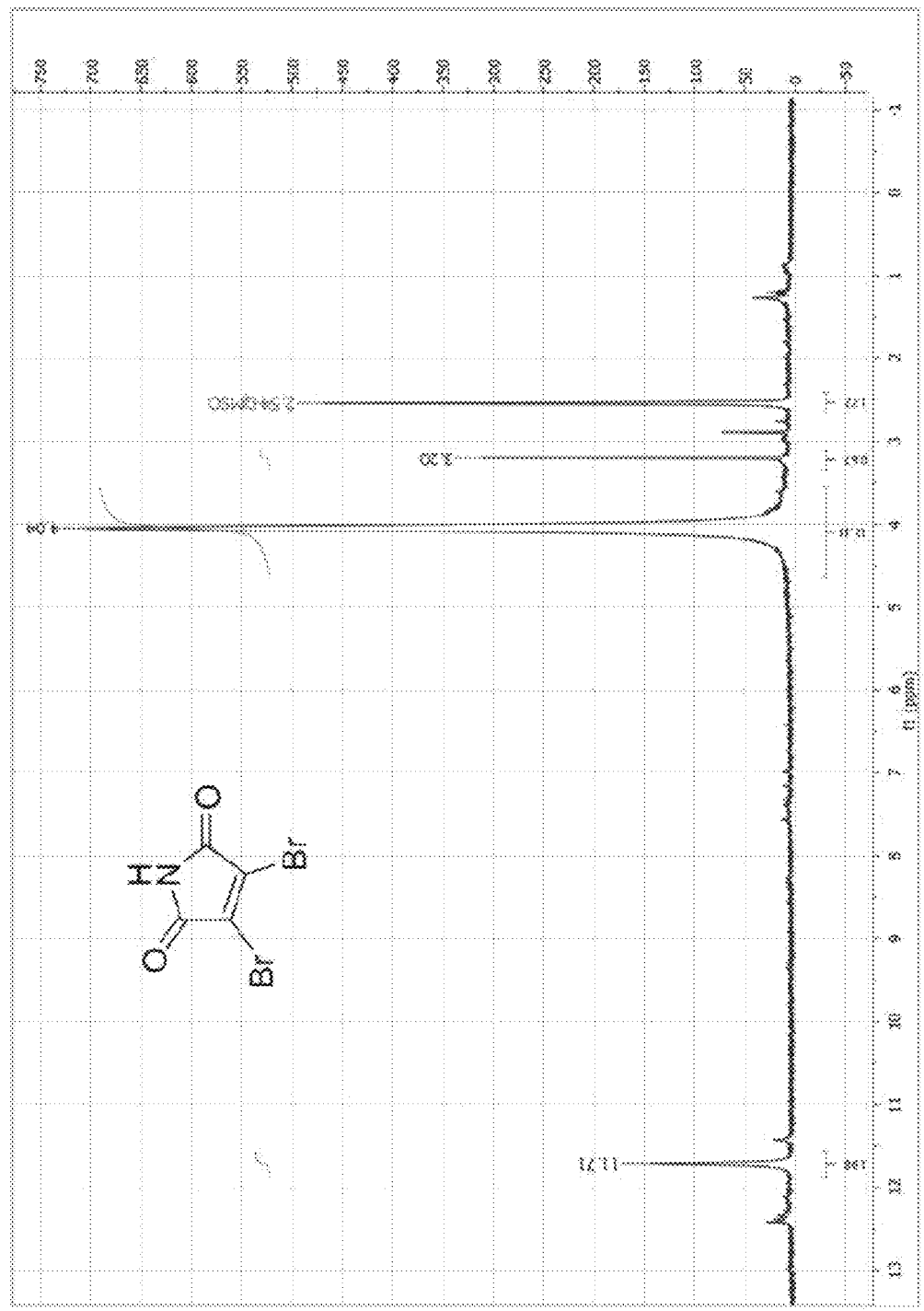
Figure 3D:
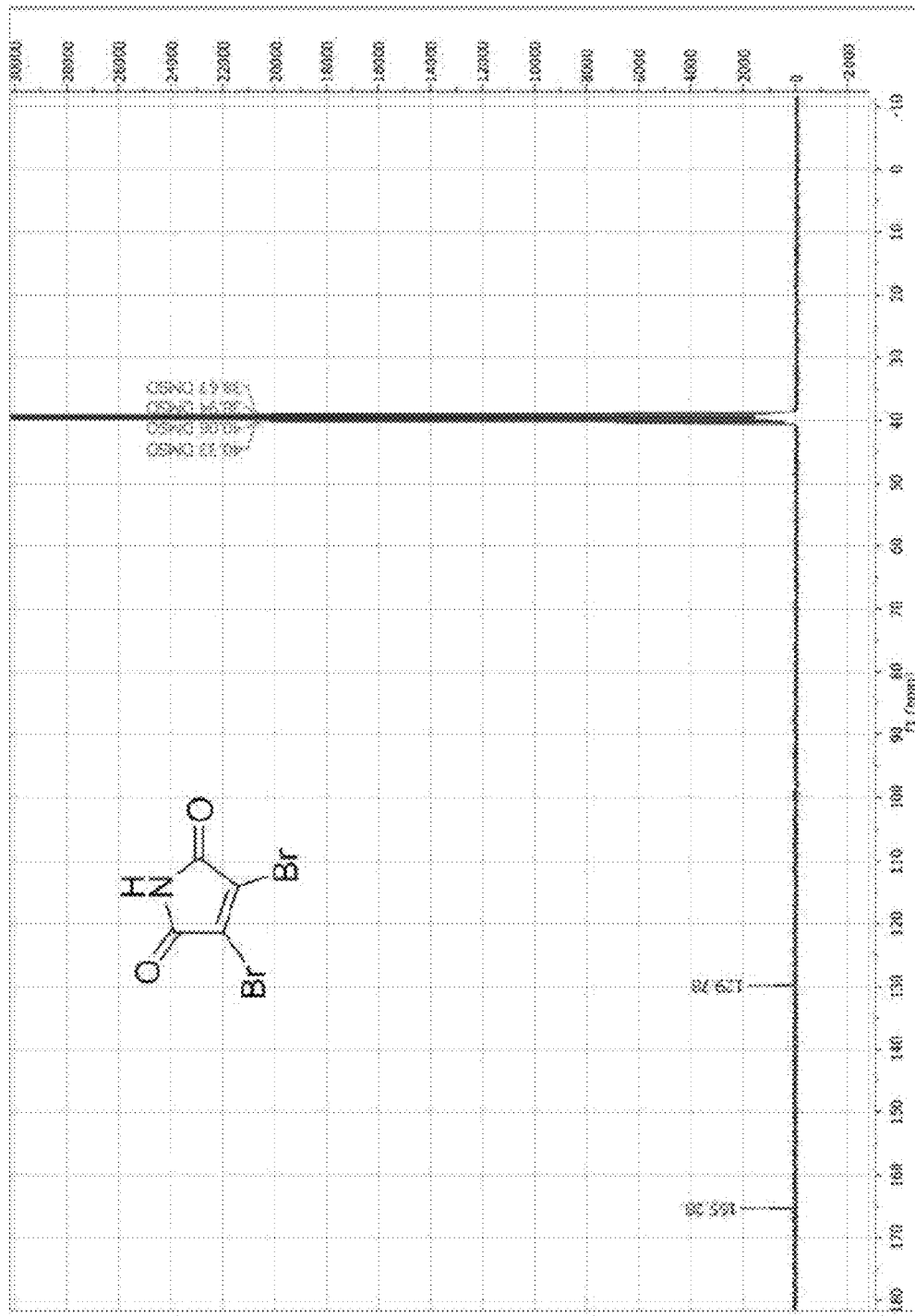
Figure 3E:
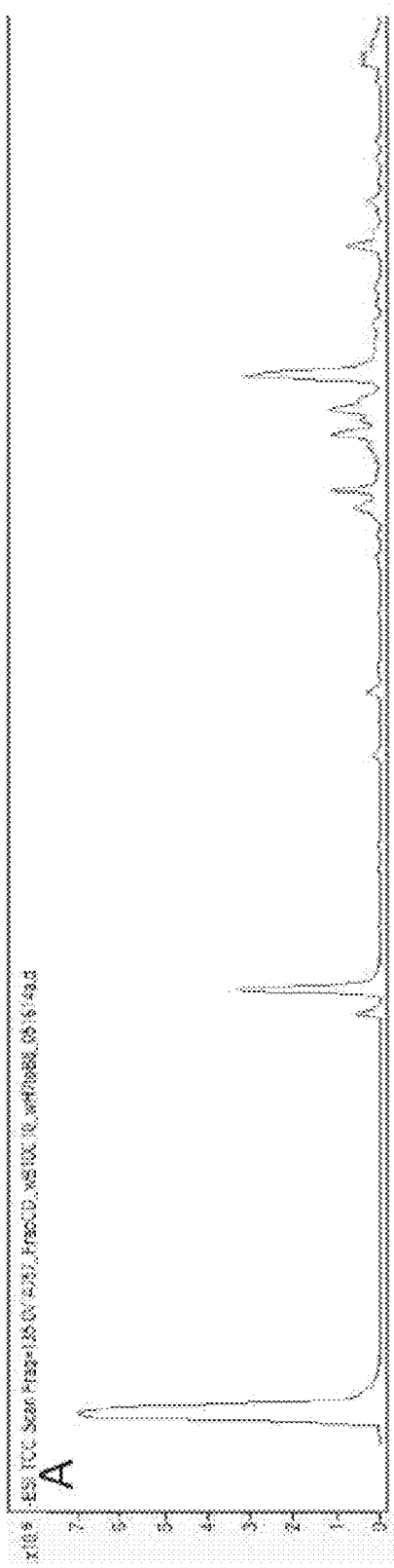
Figure 3F:
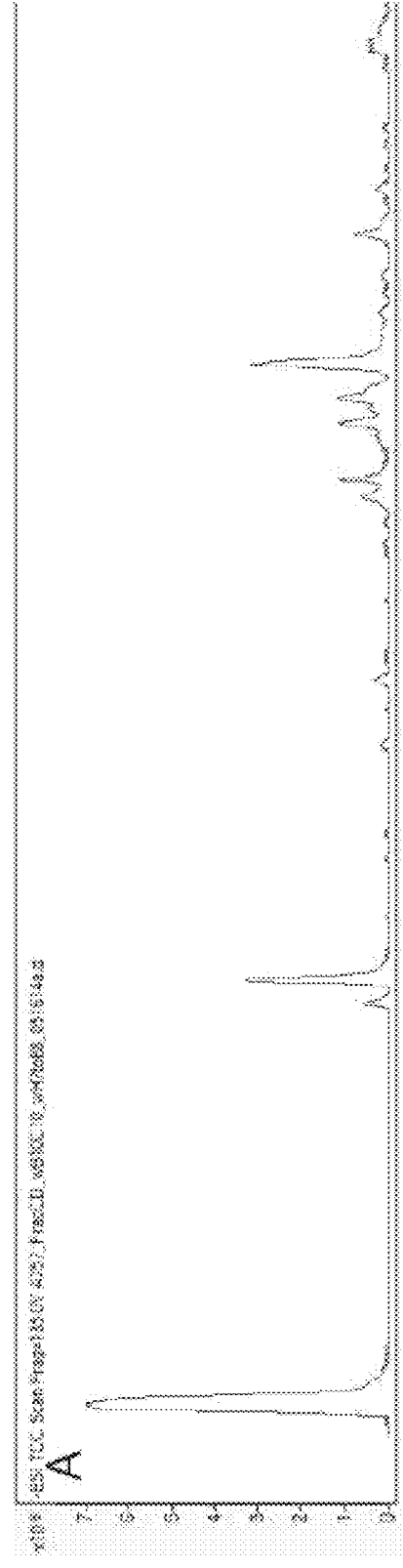
Figure 3G:
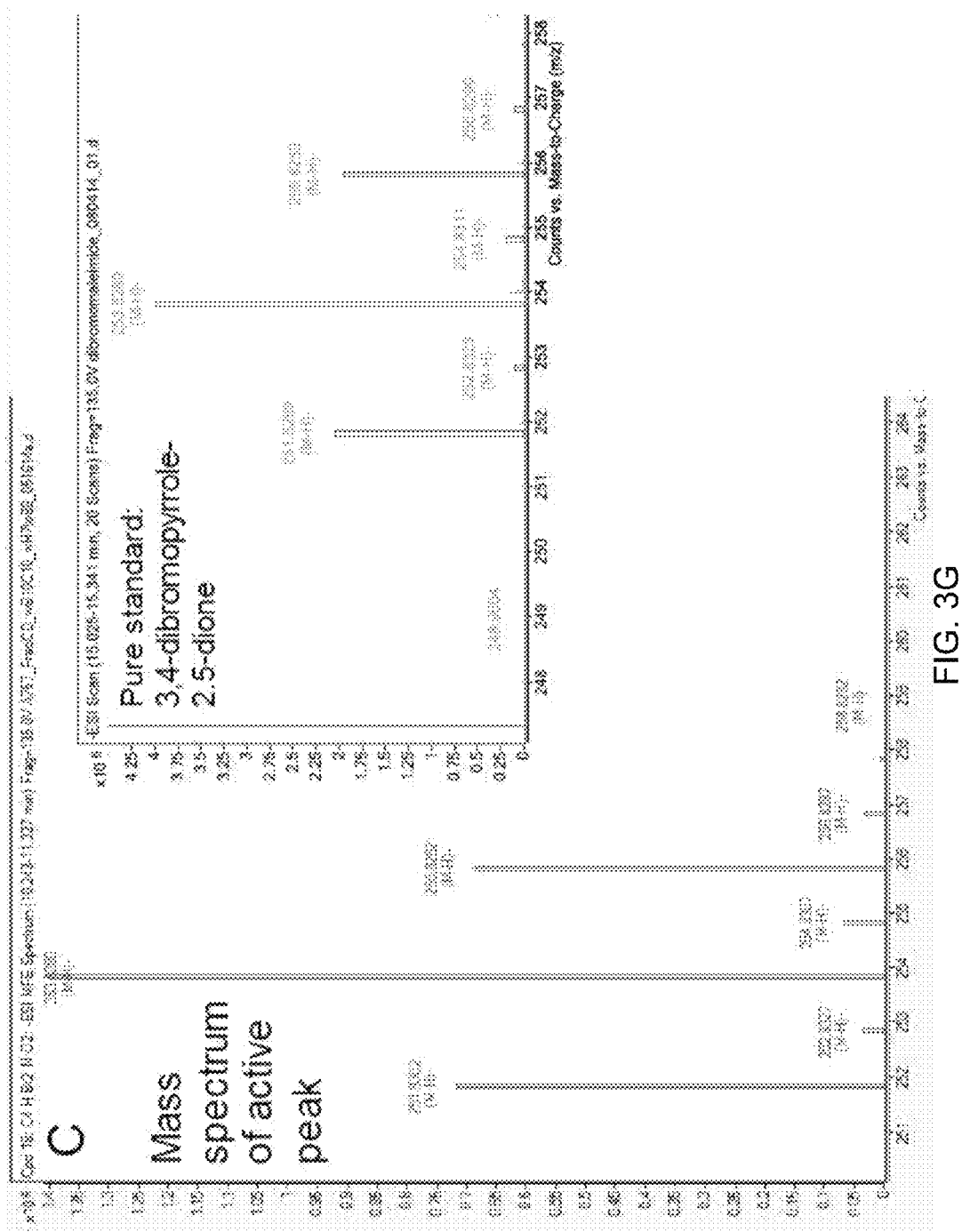

Screening features detected with an untargeted metabolomics approach (both (−)-HRESI and (+)-HRESI) against an in-house database containing previously reported *Pseudoalteromonas* metabolites indicated isolates in the in-house collection potentially produce molecules previously described for *Pseudoalteromonas* species. A potential annotation for the antibiotic 2-n-heptyl-4-quinolinol, known to also influence bacterium-phytoplankton interactions, was exclusively found within members of clade IV in both (+)-HRESI and (−)-HRESI data sets. Previous work indicated bacterial production of 2-n-heptyl-4-quinolinol is surface-dependent, and bacteria are able to generate localized zones of concentrated 2-n-heptyl-4-quinolinol on sinking or suspended particles without loss of this antibiotic to the surrounding seawater. Future studies might explore if *Pseudoalteromonas* species, falling within clade IV, express efflux pump inhibitors (EPIs), including compound 3,4-dibromopyrrole-2,5-dione and the antibiotic 2-n-heptyl-4-quinolinol, simultaneously on particle surfaces. Moreover, features matching the predicted molecular ions for the antibiotic diketopiperazine, cyclo-(phenylalanyl-4-hydroxyproline), and the antifungal isatin (1H-indole-2,3-dione) were also noted in many isolates. Clade IV may also exclusively produce the antibiotic 2-n-pentylquinolinol. Additional annotations for molecular ion matches from the in-house database included the cryptic metabolite 3-formyltyrosine-threonine dipeptide, indole-3-carboxaldehyde, the antibiotic p-hydroxybenzaldehyde, and the antibiotic p-hydroxybenzoic acid, all of which were expressed by the majority of *Pseudoalteromonas* isolates in the in-house collection. Molecular features found only in a single isolate included those matching the ions for the antifungal polyketide alteramide B from A757, the antistaphyloccocal/antivibrio compound indolmycin, Gram-negative antibiotic korormicin 1b from A345, and the diketopiperazine cyclo-(pipecolinyl-isoleucine) from A198. Molecular ions matching the antibiotic diketopiperazine cyclo-(pipecolinyl-phenylalanine) were found in A474 and A454, while features matching the calculated [M+H]$^+$ ions of the antibiotic pseudomonic acid C and the cytotoxic carboline alkaloid norharman (9H-pyrido[3,4-b]indole) appeared to be expressed in the majority of the isolates, with a few exceptions (FIG. 3B). Regardless, chemophylogenetic analysis indicated that some compounds were (i) characteristic of a particular isolate, (ii) clade specific (e.g., halogenated species, 2-n-heptyl-4-quinolinol, and 2-n-pentylquinolinol), or (iii) ubiquitous in the majority of isolates.

Increasingly, nonphotosynthetic Gram-negative bacteria (NPGNB) are being recognized as the true source of pharmaceutically relevant molecules from marine macroorganisms; however, the difficulty in culturing marine-derived strains to sufficient quantities has likely hampered intense bioprospecting efforts. Indeed, the majority (86%) of marine isolates in the in-house collection found to have MDR reversal activity in the initial screening efforts fall within the NPGNB group and have been isolated from both abiotic and biotic surfaces (FIG. 2B). The cosmopolitan marine genus *Pseudoalteromonas* (class Gammaproteobacteria), which constitutes 0.5-6% of bacterial species globally, has been found in seawater and marine sediments and epiphytically associated with marine eukaryotes and has been a prolific source of brominated compounds, including pentabromopseudilin, the first marine microbial natural product to be described. Compounds isolated from this genus function in multiple ecological roles including their involvement in chemical protection, settlement, germination, and metamorphosis of marine invertebrate and algal species, as well as more commercial uses as antifoulant, antibacterial, antifungal, and cytotoxic agents. Recent genome mining work has uncovered the biosynthetic pathways responsible for brominated pyrrole/phenol biosynthesis (bmp) (Agarwal et al. (2014), *Nat. Chem. Biol.*, 10, 640-647) indole derivatives, siderophores, polyketides, homoserine lactones, peptides (both ribosomal and nonribosomal origin), and hybrid molecules, which likely represent just the tip of the iceberg, as the number of pathways encoded in *Pseudoalteromonas* genomes eclipses the number of molecules identified thus far.

For marine bacteria, including many antibiotic-producing *Pseudoalteromonas* species (Bowman (2007), *Mar. Drugs*, 5, 220-241; Holmstrom et al. (1999) *S. FEMS Microbiol. Ecol.*, 30, 285-293) a viable strategy by these organisms may be to secrete an EPI to enhance their own antibiotic effectiveness. Previous research indicated the dominance and enriched diversity of *Pseudoalteromonas* species in biofilms could be attributed to their ability to rapidly form microcolonies and produce extracellular antibacterial compounds (Vynne et al. (2011), *Mar. Biotechnol.*, 13, 1062-1073; Rao et al. (2005), *Appl. Environ. Microbiol.*, 71, 1729-1736). The production of efflux pump inhibitors (EPIs) targeting resistance nodulation cell division (RND) pumps and other multidrug resistant (MDR) pumps may effectively disable the antibiotic resistance mechanisms of competitors allowing *Pseudoalteromonas* strains to colonize and persist in biofilms. This chemical strategy of using EPIs to enhance antibiotic potency has been previously described in plants mounting an attack against surface-associated Gram-positive bacteria. A Blastp search of all 54 *Pseudoalteromonas* species genomes available in the IMG database (https://img.jgi.doe.gov/cgi-bin/w/main.cgi) showed amino acid identities to the inner membrane RND transporters as high as 71% for AcrB, 65% for MexB, and 52% for MexY. Efflux pumps with homology to AcrB and MexB are known to be functional in *Vibrio parahemolyticus* inhabiting brackish saltwater, for example, where the VmeAB efflux pumps have been shown in vitro to exhibit bile salt and antibiotic resistance phenotypes. Although it is unclear what role, if any, the putative RND-type homologues present in *Pseudoalteromonas* species may play, it is possible that they could be aiding in moderating allelopathic interactions, as was found with antibiotic resistance and production in *Vibrio* species bacteria. Considering efflux pump inhibitors as antibiotic adjuvants among natural populations could add a new dimension to current understanding of competition between microbial populations. The data described herein show that *Pseudoalteromonas* strains indeed display niche specificity in regards to halogenated metabolite production, and further bioprospecting efforts could benefit from a focus on environments, such as biofilms, to enhance discovery of new antibiotic and EPI therapeutics.

Accession numbers for *Pseudoalteromonas* species strains identified in our screening efforts are deposited in GenBank (KM596668 through KM596703), along with metadata describing their coordinates of collection, date, sample description, and strain collection number.

The results described herein were obtained using the following methods and materials.

General Experimental Procedures

NMR spectra ($^1$H and $^{13}$C) were recorded on a Bruker Avance III 300 MHz spectrometer in DMSO-$d_6$ with the solvent ($\delta$H at 2.54, $\delta$C at 39.5) used as an internal standard. HPLC-MS experiments were accomplished using an Agilent Technologies 6230 Time-of-Flight (ToF) with a Dual Agilent Jet Stream Electrospray Ionization source, equipped with an Agilent 1260 Infinity series HPLC with a Phenomenex Kinetex 2.6 μm, $C_{18}$, 100 Angstrom, LC column (150×2.1 mm) as the stationary phase. All HPLC-MS experiments used a flow rate of 0.2 mL/min. This instrument was also equipped with Agilent Mass Hunter Workstation version B0.4.00 software. Mass spectra peak picking and alignment software MZmine 2.11 (Pluskal et al. (2010) *BMC Bioinf*, 11, 395) was used for processing mass spectra before principal component analysis with the PLS Toolbox in Matlab version 8.2.0.7. EPI isolation was accomplished using vacuum liquid chromatography (10×5 cm) with silica gel, pore size 60 Angstrom, particle size 40-75 μm (Sigma-Aldrich). All solvents used throughout the project were suitable for use with HPLC-MS, i.e., OPTIMA grade (Fisher Scientific). Semipreparative HPLC was carried out on an Agilent 1200 series HPLC equipped with an autosampler, diode array detector, quaternary pump, and 96-well plate fraction collector with a Phenomenex Luna 5 μm $C_{18}$(2), 100 Angstrom, LC column (250×10 mm) as the stationary phase. All semipreparative HPLC experiments used a flow rate of 4 mL/min. Authentic standards of 2,3,4,5-tetrabromopyrrole (Cat. L165042) and 3,4-dibromopyrrole-2,5-dione (Cat. 553603) were purchased from Sigma-Aldrich and dissolved in DMSO for use in activity assays.

Bacteria Culture and Chemical Library Production

Currently the Mincer Laboratory maintains over 2000 unique marine microbial isolates for chemical exploration. All pure cultures were cryopreserved in 10% sterile DMSO and stored at −85° C. A "starter" culture was prepared by inoculating 100 μL of frozen culture in 6 mL of TSW media (1 g of tryptone in 1 L of 75:25 natural seawater/Milli-Q water) and incubated at 23° C., 100 rpm for 3 days. In general, 1.5 L of TSY media (1 g of tryptone, 1 g of yeast extract, 75% seawater) is inoculated with 1.5 mL of "starter" culture and grown at 100 rpm for 8 days at 23° C. Twenty-four hours before culture filtration (day 7), 20 mL of a 1:1 mixture of sterile, washed Amberlite XAD-7 and XAD-16 resin was added to the cultures. On the eighth day, the resin was filtered from the bacterial culture under vacuum, desalted by rinsing with Milli-Q water, and allowed to dry overnight at room temperature. Metabolites were eluted from the resin first in 100 mL of (1:1) MeOH/CH$_2$Cl$_2$, followed by 100 mL of MeOH. This extract was then dried under vacuum centrifugation (ThermoSavant). Dried extracts were subsequently resuspended in DMSO at 100 mg/mL and stored at −85° C. until further testing in bacterial susceptibility assays.

Bacterial Susceptibility Determinations

Whole-cell assays were used to search for efflux pump inhibitors for three archetype RND efflux pumps (AcrAB-TolC, MexAB-OprM, and MexXY-OprM) known to contribute to antibiotic resistance in Enterobacteriaceae and *P. aeruginosa* clinical isolates. *Escherichia coli* strains engineered to overexpress RND transporters were generous gifts from Dr. C. Elkins (USFDA) and Dr. Y. Matsumoto (Osaka University).

Isolates used for screening included AG102 (derived from AG100; *E. coli* K-12), an isolate that overexpresses the AcrAB-TolC efflux system due to a mutation in the MarR (marR1), which increases the expression of MarA, a global regulator, which in turn results in the overexpression of AcrAB-TolC efflux system; and two *E. coli* MG1655 deletion mutants (ΔacrB ΔtolC) that have been transformed with the plasmid carrying genes mexAB-oprM (MG1655 ΔBC/pABM) and mexXY-oprM (MG1655 ΔBC/pXYM) from *P. aeruginosai*. *E. coli* strains harboring plasmids were always cultured in a medium containing 100 μg/mL ampicillin and 1 mM isopropyl β-D-1-thiogalactopyranoside (IPTG).

Minimum inhibitory concentrations (defined as the lowest concentration that results in no visible growth) of the antibiotics (chloramphenicol and erythromycin, both of which are substrates of RND pumps) were determined using a 2-fold standard microdilution method in Muller-Hinton broth (MHB) in microtiter plates as defined by the National Committee for Clinical Laboratory Standards (Andrews (2001), *Antimicrob. Chemother.* 48, 5-16) for each of the three *E. coli* strains. Bacterial susceptibility of extracts were tested in duplicate at 1 mg/mL and determined by rapid p-iodonitrotetrazolium chloride colorimetric assay in 96-well microtiter plates in a final volume of 200 μL as previously described (Kuete (2010), *Antimicrob. Agents Chemother.*, 54, 1749-1752). The INT assay evaluates if extracts have an MDR reversal effect (so-called "MIC/4", defined as reducing by at least 4-fold the antibiotic MICs). Test *E. coli* strains were grown in the presence of extract and either chloramphenicol or erythromycin at concentrations at one-fourth their MIC concentrations. Extracts that potentiated the effect of the antibiotic in one or more test strains of MDR *E. coli* were further tested (in a serial dilution series) in the presence and absence of antibiotic via the INT assay to establish if EPI-like activity was present. Wells containing MHB, inoculum, and DMSO at a final concentration of 1% served as a negative control. Phenylalanyl arginyl β-naphthylamide (PAβN, general RND pump inhibitor) was used as a positive control at 30 μg/mL in the INT assays.

Culture Production Scale-Up, Bioassay-Guided Fractionation, and Chemical Analysis Marine isolate A757 (GenBank KM596702), determined to be most closely related to *P. piscicida* by 16S rRNA gene sequences comparison, was cultured in 11×1.5 L Fernbach flasks and processed as described above, yielding a total of 1.73 g of extract. A total of 1.7 g of extract was applied to a silica gel column and eluted with a step gradient of 100% isooctane, 4:1 isooctane/EtOAc, 3:2 isooctane/EtOAc, 2:3 isooctane/EtOAc, 1:4 isooctane/EtOAc, 100% EtOAc, 1:1 EtOAc/MeOH, and 100% MeOH, yielding eight fractions. Active constituents, as determined with the INT assay against MG1655 ΔBC/pXYM, were eluted with 3:2 isooctane/EtOAc and 2:3 isooctane/EtOAc. These were further chromatographed by semipreparative HPLC (flow rate of 4 mL/min) using a gradient of $CH_3CN$ (0.1% formic acid) and $H_2O$ (0.1% formic acid). Chromatography methods were as follows: hold at 5% $CH_3CN$ for 5 min, ramp to 40% $CH_3CN$ over 5 min, hold at 40% $CH_3CN$ for 2 min, ramp to 95% $CH_3CN$ over 5 min, hold at 95% $CH_3CN$ for 7 min. Active constituents eluted at 95:5 $CH_3CN/H_2O$ and were subjected to a second round of semipreparative HPLC (ramp from 55% to 75% $CH_3CN$ over 20 min) with active constituents eluting with 70:30 $CH_3CN/H_2O$ into a 96-deep-well plate, resulting in activity spread over three wells containing 14.4 mg of material. LC-MS analysis with acidified solvents (0.1% formic acid) was performed on the active fraction with a solvent gradient of 6:94 $MeOH/H_2O$ ramping to 8:92 $MeOH/H_2O$ over 25 min, at a flow rate of 0.2 mL/min, which led to the identification of 3,4-dibromopyrrole-2,5-dione, the major component of the fraction. NMR spectra of 3,4-dibromopyrrole-2,5-dione from A757 and an authentic standard are shown in FIGS. 3A-3D.

Checkerboard Assay

To assess the interaction between different classes of antibiotics and 3,4-dibromopyrrole-2,5-dione, standard checkerboard assays were performed in which the minimum inhibitory concentrations (MICs) of antibiotics were determined in the presence of different concentrations of 3,4-dibromopyrrole-2,5-dione. Standard checkerboard titration microtiter plate assays were performed as described in Matsumoto et al. (2011), *PLoS One*, 6, e18547 and Lomovskaya et al. (2001), *Antimicrob. Agents Chemother.*, 45, 105-116 to determine the fractional inhibitory concentrations (FICs) of 3,4-dibromopyrrole-2,5-dione against various antibiotics (chloramphenicol, ciprofloxacin, erythromycin, kanamycin, levofloxacin, oxacillin, piperacillin, and tetracycline) for all three *E. coli* strains.

Hoechst Accumulation and Efflux Assay

To truly be considered an efflux pump inhibitor (EPI), the compound must increase the level of accumulation and decrease the level of extrusion of efflux pump substrates. The fluorescent DNA-binding dye Hoechst 33342 (H33342) a known substrate for RND pumps, is easily detected in the cell, can freely permeate the outer membrane, and can act as a reporter, all allowing for quantification of transport across living cells. Efflux-competent cells extrude H33342 and accumulate dye at a relatively slow rate, resulting in low levels of background fluorescence. Conversely, efflux-defective cells (e.g., presence of EPI) accumulate intracellular levels of H33342 at a higher rate, resulting in fluorescence retention. Wild-type *E. coli* K-12 strain, AG100, and AG100A, the ΔacrAB mutant, a generous gift from Dr. M. Viveiros (Universidad Nova de Lisboa, Portugal), were used in accumulation and efflux assays. Experiments were performed in microtiter plate format as previously described (Paixao et al. (2009) *J. Biol. Eng.* 3, 18; Viveiros et al. (2010), *Methods Mol. Biol.* 642, 159-172) using H33342 at a concentration that does not affect the growth of *E. coli* strains. All experiments were performed in duplicate. Heat-inactivated bacteria were used as a positive control to assess maximal dye accumulation.

For accumulation assays, in efflux-competent cells such as AG100, H33342 would be extruded resulting in low levels of background fluorescence, while the presence of a putative EPI would cause intracellular H33342 accumulation. Moreover, AG100A, engineered to lack efflux pumps, was used to confirm that 3,4-dibromopyrrole-2,5-dione was indeed targeting efflux pumps and that MDR reversal was limited to efflux pump overexpression in test *E. coli* strains. Specifically, accumulation of H33342 in AG100A cells would be unaffected by the presence of 3,4-dibromopyrrole-2,5-dione. Briefly, AG100 and AG100A were grown in Luria broth at 37° C. and 200 rpm until an $OD_{600}$ of 1.0, then pelleted at 3000 rpm for 15 min, washed twice with phosphate-buffered saline (PBS), and diluted in PBS (without glucose) to $OD_{600}$ 0.3. The following conditions were used to achieve a minimal accumulation of H33342 in AG100 and AG100A cells: the use of 2.5 μM H33342 in the presence of 22 mM glucose at 37° C. PAβN (15.6 μg/mL) was used as a positive control. Fluorescence values for wells containing media and compounds only were subtracted from those containing bacteria to control for any background fluorescence due to the presence of test compounds. Bacteria in PBS without H33342+glucose+3,4-dibromopyrrole-2,5-dione were also used as a control. Bacterial cells were allowed to incubate for ~30 min until H33342 accumulation stabilized, after which 3,4-dibromopyrrole-2,5-dione (concentrations ranging from 0.06-64 µg/mL) and PAβN (15.6 µg/mL) were added. Accumulation of H33342 was continuously monitored (Excitation 350 nm/Emission 460 nm) for another 60 min using a microplate reader (SpectraMax M2).

For efflux assays, a time-dependent decrease in fluorescence of H33342-loaded AG100 would be observed only when efflux is active, while the presence of a putative EPI would cause the retention of H33342 over time. Briefly, AG100 cells were grown, pelleted, and washed as described above, then "loaded" with H33342 (2.5 µM) and either PAβN (15.6 µg/mL) or 3,4-dibromopyrrole-2,5-dione (concentrations ranging from 1 to 64 µg/mL) under conditions that favor maximal accumulation (no glucose, 25° C.). When maximum accumulation was reached (after 60 min), bacteria were pelleted at 3000 rpm for 3 min, resuspended in ice-cold PBS, aliquoted into the microtiter plate, and exposed to corresponding concentrations of either PAβN or 3,4-dibromopyrrole-2,5-dione, with and without glucose at 37° C. H33342 efflux was continuously monitored by fluorescence at Excitation 350 nm/Emission 460 nm for an additional 30 min. Values from the "no glucose" control wells were subtracted from the values obtained from wells containing glucose. To obtain a comparative analysis of the efflux, the fluorescence data of the H33342-loaded cells were normalized to 1, thereby establishing a maximum fluorescence value.

Statistical comparisons of H33342 accumulation assay data were performed by combining fluorescence measurements from the final four time points (period where accumulation/fluorescence has stabilized) and comparing fluorescence among treatments using a one-way ANOVA with a Dunnett's post-test to determine statistical differences between treatments and the Hoechst control (Graphpad Prism 6.05). To calculate the H33342 efflux $IC_{50}$ concentration of 3,4-dibromopyrrole-2,5-dione, final fluorescence measurements (from final four data points, as described above) were used to plot efflux versus EPI concentration. The line was then fitted to a sigmoidal curve, and $IC_{50}$ was calculated in Graphpad.

Chemical Profiling with Mass Spectrometry

Exuded secondary metabolites produced by *Pseudoalteromonas* species extracts (n=36 individual strain extracts) were diluted to 5 mg/mL in DMSO for untargeted metabolomic fingerprint analysis. Standards of 2,3,4,5-tetrabromopyrrole (in a standard curve spanning 2 orders of magnitude) were used to determine the retention time and limit of detection (calculated as 3×SD/slope of regressed standard curve). Extracts were then profiled (5 µL injections) by reversed-phase HPLC/MS ToF, using MeOH (0.1% formic acid) and H2O (0.1% formic acid). Chromatography methods were as follows: hold at 5% MeOH for 5 min, ramp to 40% MeOH over 5 min, and hold for 2 min, ramp to 95% MeOH over 5 min, and hold for 3 min. The first 4.5 min of each run was not injected into the mass spectrometer to avoid DMSO contamination, and there was an 8 min column equilibrium time between injections. Column temperature was held at 35° C. with a flow rate of 0.2 mL/min.

For profiling, spectra were collected in both positive ((+)-HRESI) and negative ((−)-HRESI) ionization modes in two separate runs (i.e., no polarity switching). Settings were as follows for (+)-HRESI: mass correction ions used were 922.0098 m/z and 121.0509 m/z (injected at source); scanning a 20-3000 m/z range with a scan rate of 1.00; gas temperature and sheath gas temperature at 350° C. Drying gas flow rate was 8 L/min, while sheath gas flow rate was 10 L/min with nebulizer pressure set to 40 psi. Capillary voltage and nozzle voltages were 3500 and 1000 V, respectively. Fragmentor and skimmer voltages were 135 and 65 V, respectively. These settings were held for (−)-HRESI except for the mass correction ions used, which were 1033.9881 m/z and 112.9856 m/z in negative mode.

Metabolomics Processing and Statistical Analysis

For metabolomics analysis, individual spectra were exported from Mass Hunter Workstation as .mzData files and imported in MZmine (Katajamaa et al. (2005) *BMC Bioinf.* 6, 179) for preprocessing, as described previously (Macintyre et al. (2014), *Mar. Drugs,* 12, 3416-3448; Williams et al. (2011), *Dis. Aquat. Org.,* 94, 89-100). This included mass detection, chromatogram building, peak convolution, deisotoping, retention time normalization, spectral alignment, gap-filling, and duplicate peak filtering. The same algorithms and settings were used for both (+)-HRESI and (−)-HRESI data, except that minimal peak thresholds were set to 5000 ion counts for (−)-HRESI and 10,000 ion counts for (+)-HRESI data. After processing, a list of chemical features (m/z-retention time pairs) was filtered to include only those features greater than an order of magnitude more concentrated in a *Pseudoalteromonas* sample than in the media blank. For (+)-HRESI data, all features detected between 18.99 and 23.0 min were also removed due to contamination from polyethylene glycol during those retention times. Filtered data sets were then imported into Matlab and autoscaled (van den Berg et al. (2006), *BMC Genomics* 7, 142) before principal component analysis using the PLS Toolbox (Poulson-Ellestad et al. (2014), *Proc. Natl. Acad. Sci. U.S.A.,* 111, 9009-9014) while (+)-HRESI and (−)-HRESI data were analyzed separately. PCA was used to visualize differences among the exuded metabolite profiles of the *Pseudoalteromonas* strains. The loadings for particular principal components were examined to determine which suites of chemical features were likely to be differentially expressed in different clades of *Pseudoalteromonas*, and in particular clade IV. Mass Hunter Workstation (Qualitative Analysis) was used to confirm the presence of particular chemical features in raw (unprocessed) mass spectra and to confirm isotopic distributions of any halogenated chemical features that were important in distinguishing *Pseudoalteromonas* clade IV in the PCA. To screen for the presence of known *Pseudoalteromonas*-specific metabolites in the extracts, a literature search was performed, and previously described compounds (including their names, monoisotopic mass, and molecular formulas) were compiled into the in-house "Pseudoalteromdatabase". The feature list generated in MZmine (see above) was then searched against this database (assuming a [M−H]− adduct for (−)-HRESI or [M+H]+ adduct for (+)-HRESI) and with a mass error threshold of <5.0 ppm.

Phylogenetic Analysis

The evolutionary history was inferred using the neighbor-joining method (Saitou et al. (1987), *Mol. Biol. Evol.,* 4, 406-425) and the optimal tree is shown for topology. The percentage of replicate trees in which the associated taxa clustered together in the bootstrap test (1000 replicates) (Felsenstein (1985), *J. Evolution,* 39, 783-791) is shown next to the branches for neighbor joining (left) and maximum likelihood (right). The evolutionary history was inferred by using the maximum likelihood method based on the Kimura 2-parameter model (Kimura (1980), *M. J. Mol.*

*Evol.*, 16, 111-120). Initial tree(s) for the heuristic search of the maximum likelihood tree nodes were obtained automatically by applying neighbor-join and BioNJ algorithms to a matrix of pairwise distances estimated using the maximum composite likelihood (MCL) approach. The tree is drawn to scale, with branch lengths in the same units as those of the evolutionary distances used to infer the phylogenetic tree. The evolutionary distances were computed using the Jukes-Cantor method (Matsubara et al. (1968), *Brookhaven Symp. Biol.*, 21, 201-216) and are in units of the number of base substitutions per site. The analysis involved 73 nucleotide sequences. All positions containing gaps and missing data were eliminated. There were 399 phylogenetically informative positions in the final data set. Evolutionary analyses were conducted in MEGA6 (Tamura et al. (2013), *Mol. Biol. Evol.*, 30, 2725-2729).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of inhibiting an efflux pump in a bacteria, the method comprising contacting the bacteria with 3,4-dibromopyrrole-2,5-dione, thereby inhibiting the efflux pump.

2. A method of inhibiting proliferation of a bacteria, the method comprising contacting the bacteria with 3,4-dibromopyrrole-2,5-dione and an antibiotic, thereby inhibiting the proliferation of the bacteria.

3. A method of inhibiting survival of a bacteria, the method comprising contacting the bacteria with 3,4-dibromopyrrole-2,5-dione and an antibiotic, thereby inhibiting the survival of the bacteria.

4. A method of increasing the efficacy of an antibiotic, the method comprising contacting a bacteria with 3,4-dibromopyrrole-2,5-dione and an antibiotic, thereby increasing the efficacy of the antibiotic.

5. A method of inhibiting development of antibiotic resistance in a bacteria, the method comprising contacting the bacteria with 3,4-dibromopyrrole-2,5-dione and an antibiotic, thereby inhibiting the development of resistance to the antibiotic.

6. The method of claim 1, wherein the bacteria is Gram-positive or Gram-negative.

7. The method of claim 1, wherein the bacteria is *Escherichia coli, Salmonella, Enterobacter, Klebsiella, Neisseria,* or *Pseudomonas*.

8. The method of claim 7, wherein the bacteria is multi-drug resistant *Escherichia coli*.

9. The method of claim 1, wherein the efflux pump is a resistance nodulation cell division pump.

10. The method of claim 9, wherein the resistance nodulation cell division pump is selected from the group consisting of AcrAB-TolC, MexAB-OprM, and MexXY-OprM.

11. The method of claim 2, wherein the antibiotic is selected from the group consisting of a fluoroquinolone, aminoglycoside, macrolide, beta-lactam, tetracycline, cephalosporins, and chloramphenicol.

12. The method of claim 11, wherein the antibiotic is ciprofloxacin, levofloxacin, kanamycin, erythromycin, oxacillin, piperacillin, amoxicillin, or azithromycin.

13. The method of claim 2, wherein the method reduces the minimum inhibitory concentration of the antibiotic by at least 4-fold, 8-fold, or 16-fold.

14. The method of claim 1, wherein the method inhibits efflux from the efflux pump by at least about 75%, 85%, 95% or more.

15. A pharmaceutical composition for treating a bacterial infection comprising an effective amount of 3,4-dibromopyrrole-2,5-dione and an effective amount of an antibiotic selected from fluoroquinolone, aminoglycoside, macrolide, beta-lactam, tetracycline, cephalosporins, and chloramphenicol in a pharmaceutically acceptable excipient.

16. The pharmaceutical composition of claim 15, wherein the antibiotic is ciprofloxacin, levofloxacin, kanamycin, erythromycin, oxacillin, piperacillin, amoxicillin, or azithromycin.

17. The pharmaceutical composition of claim 15, wherein the bacterial infection is multidrug resistant.

18. A kit for treating a bacterial infection in a subject, the kit comprising an effective amount of 3,4-dibromopyrrole-2,5-dione and an antibiotic selected from fluoroquinolone, aminoglycoside, macrolide, beta-lactam, tetracycline, cephalosporins, and chloramphenicol.

19. The kit of claim 18, wherein the antibiotic is ciprofloxacin, levofloxacin, kanamycin, erythromycin, oxacillin, piperacillin, amoxicillin, or azithromycin.

* * * * *